(12) United States Patent
Iscovich et al.

(10) Patent No.: US 8,338,363 B2
(45) Date of Patent: Dec. 25, 2012

(54) PHARMACEUTICAL COMPOSITIONS COMPRISING CASEIN DERIVED PEPTIDES AND METHODS OF USE THEREOF

(75) Inventors: Jose Mario Iscovich, Gan-yavne (IL); Nissim Silanikove, Yavane (IL); Javier Iscovich, Karmei Yossef (IL)

(73) Assignees: Mileutis Ltd., Gan-Yavne (IL); State of Israel, Ministry of Agriculture & Rural Development, Agriculture Research Organization, Bet Dagan (IL)

( * ) Notice: Subject to any disclaimer, the term of this patent is extended or adjusted under 35 U.S.C. 154(b) by 0 days.

(21) Appl. No.: 13/107,331

(22) Filed: May 13, 2011

(65) Prior Publication Data
US 2011/0212886 A1 Sep. 1, 2011

Related U.S. Application Data

(62) Division of application No. 11/913,239, filed as application No. PCT/IL2006/000524 on May 2, 2006, now Pat. No. 7,968,513.

(60) Provisional application No. 60/688,697, filed on Jun. 9, 2005, provisional application No. 60/676,292, filed on May 2, 2005.

(51) Int. Cl.
*A61K 38/00* (2006.01)
*A61P 3/02* (2006.01)
*C07K 2/00* (2006.01)

(52) U.S. Cl. ......................................... 514/1.1; 514/5.7

(58) Field of Classification Search ........................ None
See application file for complete search history.

(56) References Cited

U.S. PATENT DOCUMENTS

| | | | |
|---|---|---|---|
| 3,764,670 A | 10/1973 | Katzirkatchalsky et al. | |
| 4,740,462 A | 4/1988 | Brule et al. | |
| 5,015,628 A | 5/1991 | Reynolds | |
| 5,227,154 A | 7/1993 | Reynolds | |
| 5,405,756 A | 4/1995 | Naito | |
| 5,834,427 A | 11/1998 | Han | |
| 6,391,849 B1 | 5/2002 | Shamay | |
| 6,448,374 B1 | 9/2002 | Reynolds | |
| 6,652,875 B1 | 11/2003 | Bannister | |
| 6,780,844 B1 | 8/2004 | Reynolds | |
| 7,968,513 B2 * | 6/2011 | Iscovich et al. | 514/1.1 |
| 2002/0147144 A1 | 10/2002 | Sidelman | |
| 2004/0167073 A1 | 8/2004 | Sidelman | |
| 2005/0220801 A1 | 10/2005 | Otani | |

FOREIGN PATENT DOCUMENTS

| | | |
|---|---|---|
| EP | 1375513 | 1/2004 |
| WO | 01/13739 | 3/2001 |
| WO | 2005/081628 | 9/2005 |

OTHER PUBLICATIONS

Shamay et al. Casein-derived phosphopeptides disrupt tight junction integrity, and precitpitously dry up milk secretion in goats. Life Sciences. 2002. vol. 70, pp. 2707-2719.*
Minson. The effects of feeding protected and unprotected casein on the milk production of cows grazing ryegrass. The Journal of Agricultural Science. 1981. vol. 96, pp. 239-241.*
Vik-mo et al. Milk Protein Production in Cows Abomasally Infused with Casein or Glucose, J. Dairy Sci. 1974, vol. 57, No. 8, pp. 869-877.*
Akoum et al., "Ultrafiltration of Low-Heat and UHT Skim Milks with a Shear-Enhanced Vibrating Filtration System", Separation Sci Tech. 38(3):571-589. (2003).
Andrews, "Proteinases in normal bovine milk and their action on caseins", J Dairy Res. Feb.;50(1):45-55. (1982).
Annen et al., "Effect of Modified Dry Period Lengths and Bovine Somatotropin on Yield and Composition of Milk from Dairy Cows", J. Dairy Sci. 87:3746-3761. (2004).
Capuco et al., "Mammary involution in dairy animals", J Mammary Gland Biol Neoplasia. Apr.;4(2):137-144. (1999).
Cattell et al., "Environmental gram-positive mastitis treatment: in vitro sensitivity and bacteriologic cure", J Dairy Sci. Sep.;84(9):2036-2043. (2001).
DeGraves et al., "Economics of mastitis and mastitis control", Vet Clin North Am Food Anim Pract. Nov.;9 (3):421-434. (1993).
De Noni et al., "About presence of free phosphoserine in ripened and in enzymatic hydrolyzate of casein", Nahrung. 41(5):268-273. (1997).
Eigel et al., "Nomenclature of proteins of cow's milk: Fifth revision", J. Dairy Sci. 67:1599-1631. (1984).
Fitzgerald, "Potential uses of caseinophosphopeptides", Int. Dairy J. 8(5):451-457. (1998).
Fregonesi et al., "Behaviour, performance and health indicators of welfare for dairy cows housed in strawyard or cubicle systems", Livestock Production Science. 68:205-216. (2001).
Fregonesi et al., "Influence of space allowance and milk yield level on behaviour, performance and health of dairy cows housed in strawyard and cubicle systems", Livestock Production Science. 78:245-257. (2002).
Gruet et al., "Bovine mastitis and intramammary drug delivery: review and perspectives", Adv Drug Deliv Rev. Sep. 1;50(3):245-259. (2001).
Hipp et al., "Separation of alpha-, β- and -gama Casein1", Journal of Dairy Science. 35(3):272-281. (1952).
Kuhn et al., "Dry period length to maximize production across adjacent lactations and lifetime production", J Dairy Sci. 89(5):1713-1722. (2006).
Leitner et al., "Changes in milk composition as affected by subclinical mastitis in sheep", J Dairy Sci. Jan.;87 (1):46-52. (2004).
Lemieux et al., "High performance liquid chromatography of casein hydrolysates phosphorylates and dephosphorylated, I peptide mapping", Journal of Chromatography. 519(2):299-321 (1990).

(Continued)

*Primary Examiner* — Marcela M Cordero Garcia
(74) *Attorney, Agent, or Firm* — Rodney J. Fuller; Booth Udall, PLC

(57) ABSTRACT

The present invention relates to peptides derived from casein and their use in the management of lactating animals, particularly to methods for decreasing the length of the dry period of a lactating livestock animal, for increasing its milk yield and milk hygiene after parturition and for improving the livestock welfare. The present invention further relates to pharmaceutical compositions comprising peptides derived from casein in the form of a sterile solution, which compositions are clear and substantially devoid of micelles.

37 Claims, 5 Drawing Sheets

OTHER PUBLICATIONS

Li et al., "Mammary-Derived Signals Activate Programmed Cell Death during the First Stage of Mammary Gland Involution", Proceedings of the National Academy of Sciences of the United States of America. Apr. 1;94(7):3425-3430. (1997).

Marti et al., "Milk accumulation triggers apoptosis of mammary epithelial cells", Eur J Cell Biol. Jun.;73(2):158-165. (1997).

Meggio et al., "A synthetic beta-casein phosphopeptide and analogues as model substrates for casein kinase-1, a ubiquitous, phosphate directed protein kinase", FEBS Lett. Jun. 3;283(2):303-306. (1991).

Merrifield, "Solid Phase Peptide Synthesis. I. The Synthesis of a Tetrapeptide", J. Am. Chem. Soc. 85(14):2149-2154. (1963).

Perich, "Synthesis of phosphopeptides using modern chemical approaches", Methods Enzymol. 289:245-266. (1997).

Politis I., "Plasminogen Activator System: Implications for Mammary Cell Growth and Involution", Journal of Dairy Science. 79(6):1097-1107. (1996).

Quarrie et al., "Local regulation of mammary apoptosis in the lactating goat", Biochem. Soc. Trans. 22(2):178S. (1994).

Shamay et al., "Casein-derived phosphopeptides disrupt tight junction integrity, and precipitously dry up milk secretion in goats", Life Sci. Apr. 26;70(23):2707-2719. (2002).

Shamay et al., "Infusions of Casein Hydrolyzates into the Mammary Gland Disrupt Tight Junction Integrity and Induce Involution in Cows", J. Dairy Sci. 86:1250-1258. (2003).

Silanikove et al., "Stress down regulates milk yield in cows by plasmin induced beta-casein product that blocks K+ channels on the apical membranes", Life Sci. Sep. 22;67(18):2201-2212. (2000).

Silanikove et al., "Role of xanthine oxidase, lactoperoxidase, and NO in the innate immune system of mammary secretion during active involution in dairy cows: manipulation with casein hydrolyzates", Free Radic Biol Med. 38 (9):1139-1151. (2005).

Wilde et al., "Control of milk secretion and apoptosis during mammary involution", J Mammary Gland Biol Neoplasia. Apr.;4(2):129-136. (1999).

Yamagata et al., "The economic benefit of treating subclinical *Streptococcus agalactiae* mastitis in lactating cows", J Am Vet Med Assoc. Dec. 15;191(12):1556-1561. (1987).

* cited by examiner

SEQUENCE LISTING

```
<160> NUMBER OF SEQ ID NOS: 5

<210> SEQ ID NO 1
<211> LENGTH: 5
<212> TYPE: PRT
<213> ORGANISM: Artificial sequence
<220> FEATURE:
<223> OTHER INFORMATION: Derived from mammalian casein
<220> FEATURE:
<221> NAME/KEY: MISC_FEATURE
<222> LOCATION: (1)..(3)
```

<223> OTHER INFORMATION: Modified by phosphoric acid

<400> SEQUENCE: 1

Ser Ser Ser Gly Gly
1               5

<210> SEQ ID NO 2
<211> LENGTH: 25
<212> TYPE: PRT
<213> ORGANISM: Artificial sequence
<220> FEATURE:
<223> OTHER INFORMATION: Derived from Mammalian Casein
<220> FEATURE:
<221> NAME/KEY: MISC_FEATURE
<222> LOCATION: (17)..(19)
<223> OTHER INFORMATION: Modified by phosphoric acid

<400> SEQUENCE: 2

Arg Glu Leu Glu Glu Leu Asn Val Pro Gly Glu Ile Val Glu Ser Leu
1               5                   10                  15

Ser Ser Ser Glu Glu Ser Ile Thr Arg
            20                  25

<210> SEQ ID NO 3
<211> LENGTH: 21
<212> TYPE: PRT
<213> ORGANISM: Artificial sequence
<220> FEATURE:
<223> OTHER INFORMATION: Derived from Mammalian Casein
<220> FEATURE:
<221> NAME/KEY: MISC_FEATURE
<222> LOCATION: (8)..(10)
<223> OTHER INFORMATION: Modified by phosphoric acid

<400> SEQUENCE: 3

Gln Met Glu Ala Glu Ser Ile Ser Ser Ser Glu Glu Ile Val Pro Asp
1               5                   10                  15

Ser Val Glu Gln Lys
            20

<210> SEQ ID NO 4
<211> LENGTH: 21
<212> TYPE: PRT
<213> ORGANISM: Artificial sequence
<220> FEATURE:
<223> OTHER INFORMATION: Derived from Mammalian Casein
<220> FEATURE:
<221> NAME/KEY: MISC_FEATURE
<222> LOCATION: (8)..(10)
<223> OTHER INFORMATION: Modified by phosphoric acid

<400> SEQUENCE: 4

Lys Asn Thr Met Glu His Val Ser Ser Ser Glu Glu Ser Ile Ile Ser
1               5                   10                  15

Asn Glu Thr Tyr Lys
            20

<210> SEQ ID NO 5
<211> LENGTH: 25
<212> TYPE: PRT
<213> ORGANISM: Artificial sequence
<220> FEATURE:
<223> OTHER INFORMATION: Derived from Mammalian Casein
<220> FEATURE:
<221> NAME/KEY: MISC_FEATURE
<222> LOCATION: (11)..(13)
<223> OTHER INFORMATION: Modified by phosphoric acid

<400> SEQUENCE: 5

-continued

```
Asn Ala Asn Glu Glu Glu Tyr Ser Ile Gly Ser Ser Ser Glu Ser
1               5                   10                  15

Ala Glu Val Ala Thr Glu Glu Val Lys
            20                  25
```

PHARMACEUTICAL COMPOSITIONS COMPRISING CASEIN DERIVED PEPTIDES AND METHODS OF USE THEREOF

CROSS REFERENCE TO RELATED APPLICATIONS

This application is a divisional of U.S. patent application Ser. No. 11/913,239, filed Oct. 31, 2007, now allowed, which is U.S. national stage of PCT/IL2006/000524, filed May 2, 2006, which is based on and claims the benefit of U.S. Provisional Patent Application Nos. 60/688,697, filed Jun. 9, 2005, and 60/676,292 filed May 2, 2005, the contents of each of which is expressly incorporated herein in its entirety by this reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 2,310 byte ASCII (text) file named "Seq_List" created on May 13, 2011.

FIELD OF THE INVENTION

The present invention relates to peptides derived from casein and their use in the management of lactating animals, particularly to methods for decreasing the length of the dry period of a lactating livestock animal, for increasing its milk yield and milk hygiene after parturition and for improving the livestock welfare. The present invention further relates to pharmaceutical composition comprising peptides derived from casein in the form of a sterile solution, which is clear and substantially devoid of micelles.

BACKGROUND OF THE INVENTION

Casein (CN) is the predominant protein in human and non-human mammal's milk. Casein has been characterized previously as composed of three fractions, $\alpha$, $\beta 0$ and $\gamma$, according to the electrophoretic mobility of each fraction (Hipp et al. 1952. Dairy Sci., 35:272). Today, casein is defined according to the amino acid sequences of each of the subgroups $\alpha S1$, $\alpha S2$, $\gamma$ and $\kappa$ (Engel et al.1984. J. Dairy Sci. 67:1607-1608).

Enzymatic hydrolysis of casein liberates peptides that may contribute to the health and proper development of young (FitzGerald et al., 1998. Int. Dairy J. 8:451-457) and that serve as local regulators of mammary gland function (Silanikove et al., 2000. Life Sci. 67:2201-2212; Shamay et al., 2002. Life Sci. 70:2707-2719). The serine protease, plasmin, is the predominant protease in milk and is known to produce boiling-resistant peptides (proteose-peptones) from $\beta$-casein, $\alpha$-S1 casein and $\alpha S2$-casein.

The Proteose-peptones (PPs), also known as casein phosphopeptides (CPP), constitute about a third of the whey proteins (Andrews, 1983. J. Dairy Res. 50:45-55). Plasmin in milk is found mainly in its inactive from, plasminogen, and the conversion of plasminogen to plasmin is modulated by plasminogen activators (Politis I., 1996. J. Dairy Sci. 79:1097-1107).

Casein-derived peptides have been shown to have several biological activities and applications. Studies with milk compounds demonstrated casein-related bactericidal activity. U.S. Pat. No. 3,764,670 discloses novel polypeptides derived from casein possessing antibiotic properties against microorganisms.

Immune modulating activity of casein peptides has also been observed. For example, International PCT Patent Application WO 01/13739 discloses method of potentiating the immunity of mammals and promoting the growth thereof by administering proteins containing phosphorylated amino acids such as casein phosphopeptides, directly or in food. As the immunity of the mammals is potentiated, the resistance thereof against infectious diseases is strengthened and factors inhibiting the growth thereof are eliminated, thereby promoting the growth of the mammals.

U.S. Patent Applications Publication Nos. 20020147144 and 20040167073 disclose biologically active peptides that are derived from or are similar to sequences identical to the N-terminus of the $\alpha S1$ fraction of milk casein, which are capable of stimulating and enhancing immune response, protecting against viral infection, normalizing serum cholesterol levels, and stimulating hematopoiesis.

International PCT Patent Application WO 2005/081628 discloses biologically active peptides that are derived from or are similar to sequences of the $\alpha S1$, $\alpha S2$, $\beta$- or $\kappa$-casein fractions of milk casein, capable of immune modulation and other therapeutic activities, including but not limited to stimulating and enhancing immune response, protecting against viral infection, normalizing serum cholesterol levels, and stimulating hematopoiesis. The casein-derived peptides are non-toxic and can be used to treat and prevent immune pathologies, diabetes, hypercholesterolemia, hematological disorders and viral-related diseases.

European Patent Application No. EP1375513 discloses that among the peptides derived from casein, peptides having amino acid sequences comprising plural phosphoserine residues show a strong immuno-enhancing activity. Specifically, the invention relates to an immuno-enhancing agent comprising a peptide consisting of the amino acid sequence Q1-SerP-X-SerP-Q2, wherein, SerP represents the phosphoserine residue, X represents one to three of any amino acid residues, and Q1 and Q2 are independently absent or represents at least one of any amino acid residue.

U.S. Pat. No. 6,391,849 to one of the inventors of the present invention and co-workers discloses casein-derived proteose-peptones that act as calcium chelators, and their use in controlling physiological changes in a mammary gland, including transient and persistent cessation of milk production, induction of involution and prevention, treatment and reversal of infections.

Casein phosphopeptides have been shown to possess the unique property of being able to bind macroelements such as Ca, Mg, and Fe, along with trace elements such as Zn, Ba, Cr, Ni, Co and Se, which may be solubilized in the small intestine and therefore available for absorption. As such, CPPs are used as additives in beverages and infant food, and in dental medicaments. For example, U.S. Pat. No. 5,834,427 discloses a purified casein phosphopeptide (CPP) having a novel amino acid sequence and purified casein including same. The CPP or the casein containing same has an improved ability of solubilizing minerals and absorbing thereof in animals. The CPP or the $\beta$-casein-H containing same can be added to foodstuffs, beverages, medication, cosmetics, feed in an effective amount of enhancing a mineral absorption in animals. An oral composition comprising the beta-casein H or the inventive CPP and a pharmaceutically acceptable carrier can reduce or relieve a dentinal hypersensitivity.

U.S. Pat. No. 5,227,154 discloses a method of controlling dental calculus by treating the teeth with an oral composition which comprises specific casein phosphopeptides and/or salts thereof. U.S. Pat. No. 6,652,875 discloses a formulation for the delivery of bioactive constituents to biological surfaces, including dental surfaces such as teeth and gums, wherein said formulation comprises a suspensions or solution of at least one isolated and purified casein protein or salt thereof, in water, together with at least one bioactive constituent.

Various methods for the preparation of casein hydrolyzates, specifically CPPs, have been proposed. For example, U.S. Pat. No. 4,740,462 discloses production of CPP by hydrolysis of casein with a crystalline trypsin followed by fractionation and separation by ultrafiltration or chromatographic techniques such as gel permeation chromatography or ion-exchange chromatography. This method may have some research utility, but it is not suitable or economical on an industrial scale. Other methods involve the use of toxic substances, such as barium chloride, which are not acceptable in food product and/or pharmaceutical compositions.

Regardless of the method used for preparation, a solution containing a casein hydrolyzate tends to be turbid. Turbidity is considered as a significant disadvantage in pharmaceutical compositions as well as in some food products, specifically beverages, as it is difficult or impossible to visibly track changes in the turbid composition, particularly to detect contaminations. U.S. Pat. No. 5,405,756 discloses a method for the preparation of casein phosphopeptide suitable for use as an additive to beverages without affecting the beverage transparency; however, the obtained protein contains calcium, and, moreover, a clear solution is obtained only at an acidic pH.

Management of Lactating Livestock Animals

In the modern dairy industry, lactating animals in herds go through controlled cycles of milking and pregnancy, as such regimes contribute to a significant increase in milk production. In current management of dairy herds, for example cows and goats, there is a significant overlap between lactation and pregnancy, wherein a "dry period" is imposed between 50 to 70 days prior to parturition by cessation of milking. This regime is set to compromise between the need to induce involution, a necessary process for subsequent healthy lactating period, and the requirement for high milk production all year long.

Cessation of milk removal leads to rapid changes in the mammary secretion and to initiation of the process of active mammary involution. This process comprises an extensive and highly ordered sequence of changes in tissue and milk composition, which occur during the transition between the lactating and the non-lactating states. During the first stage of mammary involution, the process is triggered by local stimuli that initiate apoptosis, but involution can be reversed by reinitiating milk removal (Capuco and Akers, 1999. J. Mammary Gland Biol. Neoplasia 4:137-144; Wilde et al., 1999. J. Mammary Gland Biol. Neoplasia 4:129-136). This local control can cause involution when milk stasis is induced in individual glands, as was observed in lactating goats following unilateral cessation of milking (Quarrie et al., 1994. Biochem. Soc. Trans. 22:178S), or in lactating mice following teat sealing (Li et al., 1997. Proc. Natl. Acad. Sci. U.S.A. 94: 3425-3430; Marti et al., 1997. Eur. J. Cell. Biol. 73:158-165).

The second stage of involution is persistent, and milk removal cannot cause resumption of milk secretion (Capuco and Akers, 1999. ibid; Wilde et al., 1999. ibid). Reversal of the second state of involution can occur only in a subsequent lactating stage after giving birth. This stage is characterized by activation of proteases that destroy the lobular-alveolar structure of the gland by degrading the extracellular matrix and basement membrane, as well as massive loss of alveolar cells.

The cessation of milking to induce involution is associated with increased risk of developing mastitis, a disease caused by intramammary infection (IMI) with pathogens, mostly bacteria, but also yeast, fungi, or even algae. Mastitis can be clinical, with local (and in some cases general) clinical signs and milk abnormalities, or subclinical with production losses and lowered milk quality.

Modern dairy cows are usually dried while still producing 20 to 40 liters of milk per day. Therefore, milk stasis may cause leaking of mammary secretion, which substantially increases the risk of acquiring IMI. Conventional dry-off, leading to a long process of involution, is typically associated with a higher rate of IMI. Clinical and subclinical mastitis produce significant economic losses due to rejected milk (less farm production), degraded milk quality (less revenue), early culling of cows (loss of genetic potential), drug costs, veterinary expenses, and increased labor costs for the farmer. Mastitis is the most debilitating disease in dairy herds, costing in the U.S. dairy industry alone about $2 billion annually.

It has previously been shown by one of the inventors of the present invention and co-workers that a pure $\beta$-casein ($\beta$-CN) fraction 1-28 down-regulates milk secretion in cows and goats. The activity of this peptide was correlated with its ability to block potassium channels in the apical membranes of mammary epithelia (Silanikove et al., 2000. supra).

It was also shown that injection of crude preparation of casein hydrolyzates (CNH) into the udder of a goat or a cow mimics the natural phenomenon of involution, inducing a local inflammatory response and loss of tight junction (TJ) integrity, followed by rapid drying-off of mammary secretion (U.S. Pat. No. 6,391,849; Shamay et al., 2002. ibid; Shamay et al., 2003. J. Dairy Sci. 86:1250-1258). The process induced by CNH was more rapid and synchronized than that induced at natural drying-off. These results indicate that it is possible to significantly reduce the time required for involution. However, it is still unclear whether it is possible to shorten or omit the dry period without affecting the milk yield in the subsequent lactation period. Annen et al. (2004. J Dairy Science 87:3746-3761), showed that treatment of multiparous cows with bovine somatotropin (bST) enabled shortening, and even omitting, the dry period without reduction in milk production; however, this treatment was not as effective for primiparous cows. Moreover, it has been previously shown that treatment with bST causes mastitis, reproductive disorders and other production related diseases, and that such treatment increases foot disorders.

Farm animal welfare is of increasing public concern in Western societies in the last decades (Broom DM 1992 In: Phillips et al., Eds. Farm Animals and the Environment. CAB Wallingford UK pp 245-253). Recent development in housing and management practices of farm animals under intensive production systems reflects the increase in moral concerns of animal welfare (Fregonesi et al., 2001. Livestock Production Sci. 68:205-216; Fregonesi et al., 2002. Livestock Production Sci. 78:245-257). Improvement of animal welfare, defined as the prevention of suffering and increasing the presence of positive feelings, or comfort is an important factor in livestock management (Broom, 1992. ibid). Measurements of impaired biological functioning, particularly those connected to decreased health and increased physiological stress responses, are used to evaluate the welfare status of farm animals.

There is an unmet need for an efficient, safe treatment for reducing the dry period in dairy herd without negatively affecting the milk yield, for increasing milk yield and hygiene and for keeping and/or improving the welfare of livestock animals. Furthermore, it would be highly advantageous to have pharmaceutical compositions in the form of clear, ready to use solution, comprising casein-derived peptides.

SUMMARY OF THE INVENTION

The present invention relates in general to the management of lactating livestock animals and to pharmaceutical compositions comprising casein-derived peptides. Particularly, the present invention relates to methods for decreasing the length of the dry period imposed on lactating animals, for increasing their milk yield and milk hygiene, and for preventing suffering associated with mammary gland infection and abrupt cessation of milking. The present invention also relates to pharmaceutical compositions comprising a therapeutically effective amount of at least one peptide derived from casein, wherein the compositions are in the form of a clear sterile solution, substantially devoid of casein micelles, and comprise peptides having a substantially uniform, low molecular weight of from about 1,000 to about 5,000 Dalton.

It is a common practice in herds maintained for milk production to enforce cessation of milk production by a lactating animal before an expected parturition. The non-lactating period, defined as the "dry period", is very important to the health of the animal and for maintaining its capability to produce milk. Hitherto, a dry period of 50 to 70 days has been the industry standard. Unexpectedly, the present invention now shows that it is possible to shorten the length of the dry period without negatively affecting the milk yield after parturition. Surprisingly, the present invention now discloses a method for increasing the milk yield after parturition as compared to the milk yield in the lactating period before parturition.

Thus, according to one aspect, the present invention provides a method for reducing the length of the dry period between cycles of lactation in a lactating animal without negatively affecting the milk yield, comprising administering to a lactating animal a therapeutically effective amount of at least one peptide derived from casein.

According to certain embodiments, the dry period is reduced to less than 50 days, preferably to less than about 40 days, more preferably to between about 20 to about 30 days.

According to another aspect, the present invention provides a method for increasing the milk yield of a lactating animal after parturition compared to the milk yield obtained in the lactating period before parturition, comprising administering to the lactating animal an effective amount of at least one peptide derived from casein.

In dairy herds, the hygiene of the milk produced, as measured by the somatic cell counts (SCC) per ml of milk, has a great influence on the profitability of the herd, as milk comprising high levels of cells per ml of milk must be discarded.

According to yet another aspect, the present invention provides a method for increasing milk hygiene of a lactating animal, comprising administering to a mammary gland of the lactating animal a therapeutically effective amount of at least one peptide derived from casein so as to reduce the somatic cell counts (SCC) in the milk as compared to the SCC before peptide administration. According to certain embodiments, the SCC after peptide administration is about 750,000 cells per ml of milk and less, preferably 600,000 cells/ml and less, more preferably 400,000 cells/ml and less, even more preferably 300,000 cells/ml of milk, most preferably 200,000 cells/ml of milk and less. According to certain embodiments, the SCC is reduced during the lactating cycle in which the treatment is applied. According to currently certain preferred embodiments, the SCC is reduced during a lactating cycle subsequent to a dry period imposed after the treatment is applied.

Mammary gland infection and/or abrupt cessation of milking cause pain and stress to the animal. Not only that such stress reduces the productivity of the suffering animal, the increased awareness to the general conditions of animals in highly intensive production systems call for methods of improving the welfare of such livestock animals. Surprisingly, the present invention now discloses that it is possible to reduce or even prevent the suffering associated with mammary gland infection or abrupt cessation of milking.

According to a further aspect, the present invention provides a method for reducing the suffering associated with mammary gland infection or abrupt cessation of milking in a livestock lactating animal, comprising administering to a mammary gland of the lactating animal a therapeutically effective amount of at least one peptide derived from casein, thereby improving the lactating animal welfare.

According to certain embodiments, improving the welfare of a lactating animal is measured by the reduction in the number of steps per day and by the prolonging the lying period per day of said animal. According to one embodiment, the at least one peptide derived from casein is administered to an infected mammary gland. According to another embodiment, the peptide or peptides are administered to a non-infected mammary gland.

According to certain embodiments, the methods of the present invention employ peptides derived from casein that are phosphopeptides. According to one embodiment, the phosphopeptide comprises the amino acid sequence Ser(p)-Ser(p)-Ser(p)-Glu-Glu (SEQ ID NO:1), and analogs or derivatives thereof. According to further embodiments, the phosphopeptide is selected from the group consisting of a phosphopeptide derived from β-casein, αS1-casein, or αS2-casein. According to certain currently preferred embodiments, the phosphopeptide employed according to the methods of the present invention comprises an amino acid sequence selected from the group consisting of SEQ ID NO:2 to SEQ ID NO:5, and analogs, derivatives or fragments thereof. According to additional currently preferred embodiments, the methods of the present invention employ a phosphopeptide consisting of an amino acid sequence selected from SEQ ID NO:2 to SEQ ID NO:5 analogs, derivatives or fragments thereof. A single peptide type as well as a plurality of peptide types can be employed.

According to certain embodiments, the methods of the present invention comprise intracanal administration of the at least one peptide derived from casein. According to certain currently preferred embodiment, the methods comprise administration into a teat canal of a mammary gland of the lactating animal. Administration to the teat canal can be by way of injection or infusion. The at least one peptide can be administered to one or more mammary glands, including concomitant administration to all mammary glands of the lactating animal. According to additional embodiments, the methods of the present invention further comprise co-administration of an anti-microbial therapy, selected from the group consisting of antibiotic, bactericide, steroidal and non-steroidal anti-inflammatory treatment, treatment with an immunomodulator and vaccination.

According to one embodiment, the method for reducing the length of the dry period between cycles of lactation comprises administering the at least one peptide derived from casein at the same time of milking cessation. Single administration as well as multiple administrations is contemplated. Typically, the peptide is administered between 1 or more times, preferably 1 to 3 times, at an interval selected from the group consisting of about 6 hours, about 8 hours, about 12 hours, about 16 hours, about 20 hours or about 24 hours. According to one currently most preferred embodiment, the at least one peptide is administered only once. According to additional embodiments, cessation of milking occurs about 60 days before an expected parturition, preferably about 40 days, more preferably between about 20 to about 30 days before an expected parturition.

According to another embodiment, the method for increasing the milk yield after parturition and during the subsequent lactating period comprises administering the at least one peptide derived from casein at the same time of milking cessation, typically about 60 days before the expected parturition, preferably about 40 days, more preferably about 30 days before parturition. Dosing and repetition of the step of administering the at least one peptide are selected so as to obtain an increase in milk yield after parturition. According to certain embodiments, the peptide is administered to at least one mammary gland between 1 or more times, typically 1 to 3 times, at an interval selected from the group consisting of about 6 hours, about 8 hours, about 12 hours, about 16 hours, about 20 hours or about 24 hours. According to one currently most preferred embodiment, the at least one peptide is administered only once. According to additional currently preferred embodiment, the peptide is administered to all four mammary glands of an udder. According to certain embodiments, the average increase in milk yield is at least about 3%, preferably at least about 6%, more preferably at least about 9%, most preferably between about 10% to about 25%.

According to yet further embodiments, an increase in milk hygiene is obtained by administering the at least one peptide derived from casein at the beginning of the dry period, typically about 60 days before an expected parturition. Dosing and repetition of the step of administration into the mammary gland are selected so as to reduce the SCC and obtain an increase in the milk hygiene at the lactating period subsequent to said dry period. According to one currently most preferred embodiment, the at least one peptide is administered only once.

According to additional embodiments, the method for preventing the suffering associated with mammary gland infection or abrupt cessation of milking comprises a single administration of the casein-derived peptide or peptides.

During the course of investigation of the novel methods disclosed in the present invention, the inventors recognized the need for improved compositions comprising casein-derived peptides.

Peptides derived from casein, which are typically hydrolyzed enzymatic digests of casein, are known for their nutritional value and as such are used in clinical nutrition, in infant food formulas and as protein enrichment of food and beverages. Casein hydrolyzates are also suggested to have pharmaceutical applications. Such preparations are commonly marketed as a dried powder for constitution with a suitable vehicle, e.g., sterile water, immediately before use. The obtained solution is amenable to contamination, due to its high nutritional value, while its turbidity interferes with instant identification of the contamination. Moreover, the turbid preparations tend to have precipitates.

Unexpectedly, the inventors of the present invention have discovered that further filtration of a turbid casein preparation through a filter of from about 0.1 micron to about 0.5 micron, preferably through a filter below 0.25 micron, substantially removes the casein micelles, the presence of which is the main cause of turbidity. Furthermore, after the filtration, the composition comprises peptides in the range of from about 1,000 Dalton to about 5,000 Dalton. This size range comprises a preferred population of casein-derived peptide, specifically phosphopeptides, such that the filtration process further provides for a composition comprising substantially uniform casein-derived peptide having a molecular weight in the range of 1,000 to 5,000 Dalton.

According to yet another aspect, the present invention provides a pharmaceutical composition comprising a therapeutically effective amount of at least one peptide derived from casein wherein the composition is in the form of a clear, ready to use sterile solution, substantially devoid of micelles, having a pH above 6.0. According to certain embodiments, the composition comprises a therapeutically effective amount of at least one phosphopeptide derived from casein. According to additional embodiments, the peptide or peptides have a molecular weight of from about 1,000 to about 5,000 Dalton, preferably about 2,500 Dalton.

It is to be understood that although the pharmaceutical compositions of the present invention were obtained by the above-described filtration, they may be obtained by any method known in the art for removing substances of above about 0.25 μm and/or peptides of above 5,000 Dalton, such as ultrafiltration, dialysis and the like.

According to one embodiment, the phosphopeptide derived from casein comprises the amino acid sequence Ser (p)-Ser(p)-Ser(p)-Glu-Glu (SEQ ID NO:1), and analogs or derivatives thereof, having a molecular weight in the range of 1,000-5000 Daltons. According to further embodiments, the pharmaceutical composition comprises a therapeutically effective amount of a phosphopeptide selected from the group consisting of a phosphopeptide derived from β-casein, a phosphopeptide derived from αS1-casein, a phosphopeptide derived from αS2-casein or a combination thereof. According to certain currently preferred embodiments, the phosphopeptide derived from β-casein comprises an amino acid sequence as set forth in SEQ ID NO:2 and analogs, derivatives or fragments thereof. According to additional currently preferred embodiments, the phosphopeptide derived from αS1-casein comprises an amino acid sequence as set forth in SEQ ID NO:3 and analogs, derivatives or fragments thereof. According to yet other currently preferred embodiments, the phosphopeptide derived from αS2-casein is selected from a peptide comprising an amino acid sequence as set forth in SEQ ID NO:4 and a peptide comprising an amino acid sequence as set forth in SEQ ID NO:5 and analogs, derivatives or fragments thereof. According to further embodiments, the pharmaceutical composition comprises a plurality of peptides derived from casein as described hereinabove. According to one embodiment, the pharmaceutical composition comprises a therapeutically effective amount of a peptide consisting essentially of an amino acid sequence as set forth in any one of SEQ ID NO:2, SEQ ID NO:3, SEQ ID NO:4, SEQ ID NO:5 or analogs, derivatives and fragments thereof or any combination thereof, having a molecular weight in the range of from about 1,000 to about 5,000 Dalton.

The peptide derived from casein can be obtained by hydrolysis of casein, or it can be a synthetic peptide. Synthetic peptides can be prepared as described hereinbelow and as is known to a person skilled in the art.

According to one embodiment, the protein content of the pharmaceutical composition of the present invention is from about 10 ng/ml to about 15 mg/ml. This amount is effective in therapeutic applications, while the solution is clear. According to one embodiment, the turbidity of the composition is less than 6 Nephelometric Turbidity Units (NTU). According to another embodiment, the pH of the composition is from about 6.0 to about 8.0.

The phosphopeptides within the compositions of the present invention are highly stable within a wide temperature range. According to one embodiment, the phosphopeptides are resistant to heating, such that no activity loss is observed when the composition comprising the peptides is heated to 50° C. to 70° C. for 10-15 min. According to another embodiment, the phosphopeptides are resistant to freezing, such that the composition may be stored at −20° C. for at least 6 months, preferably for at least 12 months.

According to another aspect, the present invention provides a pharmaceutical composition comprising a therapeutically effective amount of at least one peptide derived from casein in the form of a lyophilized powder, wherein the powder is reconstituted to a liquid before use to form a clear solution, substantially devoid of micelles and having a pH above 6.0.

It should be understood that the novel pharmaceutical compositions of the present invention, comprising at least one casein-derived peptide, particularly casein-derived phosphopeptide, which are in the form of a clear sterile solution are suitable for use in the novel methods for livestock management described hereinabove. Alternatively, these pharmaceutical compositions can be also used for any use of such peptides as described in the background section hereinabove and as are known in the art.

According to additional aspect, the present invention provides a pharmaceutical composition comprising a therapeutically effective amount of at least one peptide derived from casein wherein the composition is in the form of a clear, ready to use sterile solution, substantially devoid of micelles, having a pH above 6.0, for treating a mammary gland of a lactating animal. According to certain embodiments, the composition comprises a therapeutically effective amount of a phosphopeptide derived from casein. According to additional embodiments, the phosphopeptides within the pharmaceutical composition have an average molecular weight from about 1,000 Dalton to about 5,000 Dalton. According to a certain currently preferred embodiment, the average molecular weight is about 2,500 Dalton.

The novel pharmaceutical compositions of the present invention are surprisingly efficient in treating a mammary gland in any lactating animal, including human; livestock animals grown for meat or milk production including cows, goats, sheep, and buffalos; other livestock animals including camels, llamas, horses and pigs; and pets including cats and dogs.

According to certain embodiments, the treatment is selected from the group consisting of inducing a transient cessation of milk production, inducing a persistent cessation of milk production or inducing involution. Advantageously, the pharmaceutical compositions of the present invention induce an involution within around 3 days, without negatively affecting re-constitution of the mammary gland tissues towards the next lactating period. Moreover, involution can be induced at any stage of the lactation cycle, including at the peak of lactation.

According to yet another aspect, the novel pharmaceutical composition of the present invention is useful for prevention and treatment of microbial infection and reversal of microbial infection.

The compositions are effective in treating infections caused by a wide-range of pathogens, including, but not limited to, gram positive as well as gram-negative bacteria, fungi, mycoplasma and viruses. According to one embodiment, the compositions of the present invention are effective in treating microbial infections that cause mastitis. Thus, the pharmaceutical compositions provided by the present invention reduce the dependency on antibiotics for the treatment of infections, including mammary gland infections, alleviating both the problem of antibiotic resistant infections and the problem of antibiotic residues present in the milk in the case of mastitis. Alternatively, the pharmaceutical compositions of the present invention can be administered in combination with additional anti-microbial therapy. According to one embodiment, the pharmaceutical composition of the present invention is administered in combination with an anti-microbial agent selected from the group consisting of an antibiotic, a bactericide, a steroidal anti-inflammatory agent and a non-steroidal anti-inflammatory agent. The combination therapy can reduce the required dose of the aforementioned agent and/or enhance its therapeutic effect. According to another embodiment, the pharmaceutical composition is administered in combination with a vaccine. According to a further embodiment, the pharmaceutical composition is administered in combination with an immunomodulator.

In addition of being efficient in treating mastitis during lactation, the novel pharmaceutical compositions of the present invention successfully overcome the problem of persistence of mastitis infection from one lactation cycle to the next, when administered at the same time of inducing a dry period.

The novel pharmaceutical composition of the present invention is typically formulated for parenteral administration. According to one embodiment, the pharmaceutical composition is formulated for intracanal administration, for example by infusion or by injection. According to one currently preferred embodiment, the pharmaceutical composition is formulated for injection into a gland cistern through a teat canal of the mammary gland of the lactating animal. The pharmaceutical composition may be also formulated for topical application to a breast or udder as a gel, ointment, cream, emulsion or sustained release formulation including a transdermal patch. Alternatively, the pharmaceutical compositions of the present invention are formulated for systemic oral administration.

According to a further aspect, the present invention provides a pharmaceutical composition comprising a therapeutically effective amount of at least one peptide derived from casein wherein the composition is in the form of a clear, ready to use sterile solution, substantially devoid of micelles, having a pH above 6.0, for a use selected from the group consisting of, but not limited to, a dental use and a therapeutic use. These known uses are disclosed, for example, in U.S. Pat. Nos. 5,227,154; 5,834,427 and 6,652,875; European Patent Application No. EP1375513; International PCT Applications WO01/13739 and WO 2005/081628; and U.S. Patent Applications Publication Nos. 20020147144 and 20040167073, among others.

According to yet a further aspect, the present invention provides a method for treating a mammary gland in a lactating animal, comprising the step of administering to the lactating animal a pharmaceutical composition comprising a therapeutically effective amount of at least one peptide derived from casein, wherein the composition is in the form of a clear, ready to use sterile solution, substantially devoid of micelles, having a pH above 6.0.

According to one embodiment, the treatment is selected from the group consisting of inducing transient cessation of milk production, persistent cessation of milk production and inducing involution.

According to still further aspect, the present invention provides a method for treating and inhibiting a microbiological infection.

According to certain embodiments, the infection is mastitis, including subclinical as well as clinical mastitis and the composition is administered to an infected mammary gland of a lactating animal. According to one embodiment, the pharmaceutical composition is administered during a lactating period as to treat mastitis during milking. According to another embodiment, the pharmaceutical composition is administered at the end of a lactation cycle or during the dry period. Administration at the onset and during the dry period contemplates administration to an infected mammary gland as to treat existing mastitis as well as to non-infected mammary gland as a prophylactic treatment.

Simultaneous cessation of milking from all mammary glands of a lactating animal typically results in an undesired inflammatory reaction. Surprisingly, the present invention now shows that administering the pharmaceutical compositions of the invention to all mammary glands of a lactating animal at the same time is not accompanied with any adverse effects. Thus, it is possible to induce cessation of milk production and involution and to treat mastitis in any desired number of mammary glands of an individual animal. Administration according to the present invention includes administration to from only one gland to all glands, for example in all four glands of a cow's udder.

Application regimes of the pharmaceutical composition of the present invention depend on the desired outcome and the animal treated. A single administration as well as multiple administrations is contemplated. According to certain embodiments, for treating mastitis, the peptide is administered between 1 or more times, preferably 1 to 3 times, at an interval selected from the group consisting of about 6 hours, about 8 hours, about 12 hours, about 16 hours, about 20 hours or about 24 hours. According to other embodiments, for the induction of cessation of milk production and involution, the peptide is administered as a single treatment. A regime of single administration is highly desirable as it increases treatment compliance.

According to additional aspect, the present invention provides a method for modulating an immune response in a subject, comprising the step of administering to a lactating animal a pharmaceutical composition comprising a therapeutically effective amount of at least one peptide derived from casein, wherein the composition is in the form of a clear, ready to use sterile solution, substantially devoid of micelles, having a pH above 6.0.

According to one embodiment, modulating an immune response comprises stimulating and enhancing the innate immune response.

Other objects, features and advantages of the present invention will become clear from the following description and drawings.

DETAILED DESCRIPTION OF THE INVENTION

Figure 1:
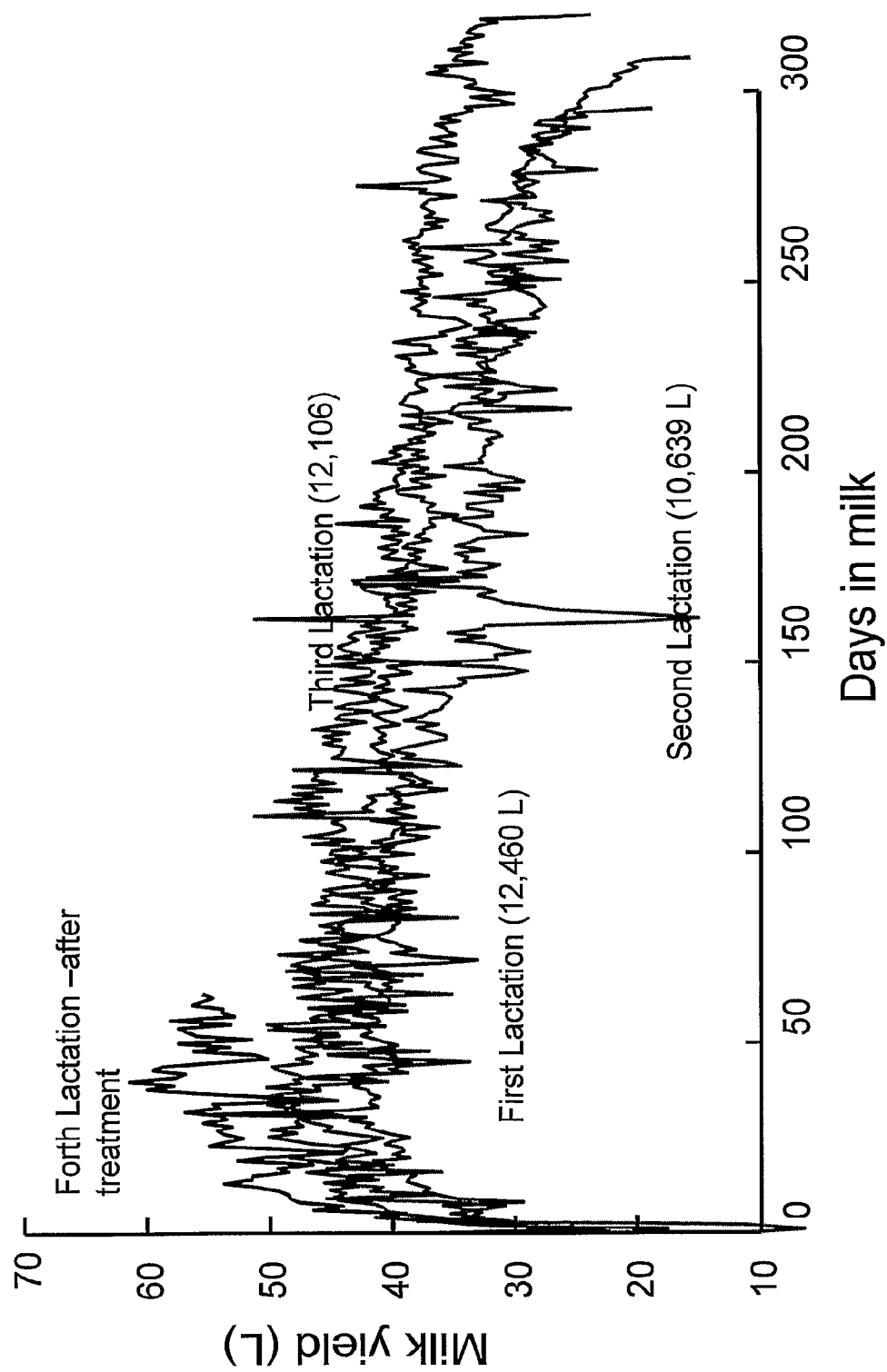
FIG. 1 shows the increase in milk production of cow No. 2425 after administration of casein hydrolyzate compared to previous lactation periods.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Definitions

As used herein, the term "casein" refers to the predominant protein in non-human mammals and human milk, comprising the subgroups $\alpha S1$, $\alpha S2$, $\beta$ and $\kappa$.

As used herein, the term $\alpha S1$, $\alpha S2$ and $\beta$-casein refers to $\alpha S1$, $\alpha S2$ and $\beta$-casein protein of a mammal, including, but not limited to, livestock mammals (e.g., cow, sheep, goat, mare, camel, deer and buffalo) human beings and marine mammals.

The term "peptide" is used throughout the specification to designate a linear series of amino acid residues connected one to the other by peptide bonds. The peptide according to the principles of the present invention is other than the intact protein.

As used herein, the term "phosphopeptide" designates a phosphorylated peptide in form of a conjugated peptide in which the non-peptide portion is a residue of phosphoric acid. In particular the expression "casein phosphopeptide" or "CPP" designates a phosphopeptide containing a casein fragment.

As used herein, the term "cessation of milk production" refers to transient cessation as well as to persistent cessation of milk production. Transient cessation of milk production refers to reversible cessation. Persistent cessation refers to interruption in lactation which is reversible only by parturition following pregnancy and by sexual hormonal treatment. According to the teaching of the present invention, mechanical stimuli (i.e., milking) can also reverse a persistent cessation of milk production induced by the compositions and methods of the invention.

As used herein the term "dry period" refers to the phase before parturition in which milking is ceased. According to present practices, applying a dry period is necessary to complete the process of involution, after which the milk secretion capacity is restored toward parturition. Currently, the length of dry period is between 50 to 70 days. Surprisingly, the present invention now shows that the length of the dry period can be reduced to less than about 50 days, preferably to less than about 40 days, more preferably to between about 20 days to about 30 days without negatively affecting the milk yield. Surprisingly, the present invention shows that application of casein-derived peptide to impose a dry period result in a significant increase in the milk yield in a lactating period subsequent to the dry period.

As used herein the term "mastitis" refers to an inflammation of a mammary gland or an udder, caused by a physical injury, introduction of chemicals, viruses, fungus, parasites or, most commonly, bacterial invasion and their toxins. "Mastitis" is used to describe all forms of such inflammation, including subclinical and clinical mastitis, clinical mastitis including mild, sever and chronic mastitis.

In subclinical mastitis, no swelling of the breast or udder is detected nor is there observable abnormalities in the milk. Special screening tests, however, such as the California Mastitis Test (CMT), Wisconsin Mastitis Test (WMT) based on an estimation of somatic cell counts and the catalase test will show changes in the milk composition. This type of mastitis is commonly referred to as "hidden."

Clinical mastitis can be mild or acute, and is characterized by the presence of leukocytes in the milk. Mild clinical mastitis involves changes in the milk appearance including presence of flakes or clots, watery milk or other unusual forms of the milk. Mild clinical mastitis may be accompanied by other symptoms including hot, sensitive or swollen breast or udder.

Severe clinical mastitis involves the symptoms of hot, sensitive, firm breast or udder that is quite painful to the lactating animal. The onset of severe clinical mastitis is sudden and the lactating animal may become ill showing signs of fever, rapid pulse, depression, weakness and loss of appetite. When the whole lactation system of the animal is affected, the condition is referred to as acute systemic mastitis. The severe symptoms may be also accompanied with cessation of milk production.

Chronic mastitis is persistent udder infection, typically in the form of subclinical mastitis, which occasionally can develop into the clinical form and back to the subclinical form. Chronic mastitis is characterized by hard lump within the mammary gland due to the establishment of bacteria and the formation of connective tissue.

As used herein, the terms "dry cow therapy" or "dry therapy" refer to a therapy administered intra-mammary immediately after the last milking in a lactation period as to eliminate, treat and cure diagnosed mastitis inflammation at the end of the lactation period.

As used herein, the term "dry cow preventive/prophylaxis therapy" refers to a therapy administered intra-mammary immediately after the last milking in a lactation period as to prevent mastitis inflammation during the dry period, and after parturition during the next lactating period.

As used herein, the term "livestock welfare" or "welfare in animal farm" refers to the prevention of suffering and increasing the presence of positive feelings, usually called comfort or pleasure, resulting from, inter alia, an increase lying periods, an increase in ruminating time, a decrease in metabolic need, a decrease in udder pressure and/or teat leakage, decrease in incidence of mastitis and other diseases, and decrease in lameness effect due to high milk yield.

As used herein, the terms "clear pharmaceutical composition", and/or "clear solution" refer to a liquid solution having a turbidity value of less than 6 NTU. As used herein, turbidity is a unit of measurement quantifying the degree to which light traveling through the water column is scattered by the suspended organic and inorganic particles. The scattering of light increases with a greater suspended load. Turbidity is commonly measured in Nephelometric Turbidity Units, which replaces the Jackson Turbidity Unit (JTU). The nephelometric method compares the scattered light by the sample and the light scattered by a reference solution.

As used herein, the terms "micelle" or micelles" refer to a molecular aggregate that constitutes a colloidal particle, particularly to casein micelles that contain mainly protein, calcium and phosphate. The micelles also contain citrate, minor ions, lipase and plasmin enzymes, and entrapped milk serum. Casein micelles are rather porous structures, occupying about 6-12% of the total volume fraction of milk. The casein micelles diameter ranges from 90 to 150 nm. Evidence from electron microscopy and other means suggest that the micelles are composed of smaller units called submicelles having diameters of from 10 to 20 nm.

As used herein, the term "sterile" refers to a solution which is pathogen free, as determined by a conventional sterility test as is known to a person skilled in the art, and endotoxin free, wherein the endotoxin level in the final product is less than 0.5 EU/ml according to the Limulus Amebocyte Lysate (LAL) test.

As used herein, the term "average molecular weight" refers to the mean plus or minus standard deviation of the molecular weight of the peptide or protein as measured by a method known to a person skilled in the art. Such methods include, for example, SDS-gel electrophoresis and size exclusion chromatography in an apparatus such as HPLC, wherein the sample is run against standards with known molecular weight.

The peptides in the pharmaceutical compositions of this invention preferably have an average molecular weight of from about 1,000 to about 5,000 Dalton. Thus, the invention particularly contemplates peptides having between 10-50 amino acid residues in total. The present invention also contemplates proteins in which the core motif sequence, e.g. the amino acid sequences set forth in SEQ ID NO:1, is artificially implanted within a sequence of a polypeptide, such as peptides manufactured by recombinant DNA technology or by chemical synthesis. The peptides can be obtained by hydrolysis of casein to yield a mixture of peptides. According to the teaching of the present invention, a mixture of the peptides can be used, or the mixture can be further purified by any protein purification method known in the art to obtain the isolated peptides.

The peptides in the pharmaceutical compositions of the present invention can also be synthesized using methods well known in the art including chemical synthesis and recombinant DNA technology. Synthesis can be performed in solution or by solid phase peptide synthesis as described by Merrifield (see J. Am. Chem. Soc., 85:2149, 1964). Phosphorylation of the Serine residues can be performed by any method as is known in the art, as described for example in Meggio et al., 1991. FEBS Lett. 283(2):303-306 and Perich J W 1997. Method Enzymol. 289:245-246, among others.

In general, peptide synthesis methods comprise the sequential addition of one or more amino acids or suitably protected or derivatized amino acids to a growing peptide chain. Normally, either the amino or the carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth; traditionally this process is accompanied by wash steps as well. After all of the desired amino acids have been linked in the proper sequence, any remaining protecting groups (and any solid support) are removed sequentially or concurrently, to afford the final peptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide, and so forth.

The present invention discloses methods for the general management of a herd of livestock lactating animals, which methods utilize casein-derived peptides.

According to one aspect, the present invention provides a method for reducing the length of the dry period between cycles of lactation without negatively affecting the milk yield, by administering to a lactating livestock animal an effective amount of at least one peptide derived from casein.

In the modern dairy industry, the lactating animal gives birth once a year, such that milking continues while the animal is pregnant. Imposing the dry period on a lactating animal before parturition is a practice taken to induce the process of involution in the mammary gland, so as to enable the restoration of the mammary tissue towards the next lactating period. Inducing the dry period is necessary, inter alia, to maintain similar milk yield before and after parturition. In cows, the natural process of involution is completed 21 to 30 days after its induction by cessation of milking. Thus, dry periods of 50 to 70 days have been an industry standard, as dry periods of less than 40 days have resulted in reduced milk yield in the subsequent lactation by 10% to 30%. Recently, it has been shown in cows that a dry period of 30 days can also take place with no loss in milk production, however, only for multiparous cows, using bovine somatotropin that may have undesired side effects (Annen et al., ibid). It has been previously shown by an inventor of the present invention and co-workers that the length of the involution process can be reduced to about 3 days in lactating goats and cows. The present invention now shows that surprisingly, it is possible to induce involution in all four mammary glands of an udder of a lactating cow within 3 days.

The present invention now discloses that administration of casein-derived peptides is efficient not only in inducing a fast involution but also in shortening the dry period to less than 50 days, preferably less than about 40 days, more preferably to between about 20 to about 30 days without negatively affecting the milk yield. Modern dairy cows are usually dried while still producing 20 to 40 liters of milk per day. Thus, shortening the dry period has a significant economic value. Moreover, the present invention now demonstrates that initiating the dry period in a lactating animal by the method of the present invention, i.e. by the administration of at least one peptide derived from casein to the lactating animal rather than by cessation of milking, results in an increase in the milk yield during the milking period subsequent to the dry period. Without wishing to be bound to a specific mechanism, this increase may be related to (a) a decrease in SCC and their negative effects on milk yield, and/or (b) a more extensive replacement of mammary epithelial cell population with new cells as a results of the more extensive apoptosis induced by the administration of the at least one peptide derived from casein.

According to another aspect, the present invention provides a method for increasing milk hygiene of a lactating livestock animal, comprising administering to a mammary gland of the lactating animal a therapeutically effective amount of at least one peptide derived from casein.

As used herein, the term "milk hygiene" refers to the somatic cell count (SCC) per ml of milk. "Increasing milk hygiene" refers to reducing the SCC to equal or less than 750,000 cells per ml of milk, preferably equal or less than 600,000 cells per ml of milk, more preferably equal or less than 400,000 cells per ml of milk, even more preferably equal or less than 300,000 cells per ml of milk, most preferably equal or less than 200,000 cells per ml of milk. A typical phenomenon of modern dairy farming is high milk yield obtained from a lactating animal, specifically a cow, albeit subclinical infection of the udder. Such a cow frequently produces a high amount of milk, however, the infection in one or more glands increases the SCC in the milk to a level that may increase the overall counts in a collecting tank, thus reducing the grading of the milk on the farm level. Antibiotic therapy applied intramammary during lactation has been shown to result in bacterial cure; however, it did not reduce quarter or cow SCC in comparison to the pre-treatment levels (Cattell et al., 2001. J. Dairy Sci. 84:2036-2043). The present invention now shows that administering casein derived peptides results in a significant decrease in the SCC. Surprisingly, the present invention now discloses that a single administration of at least one casein-derived peptide is sufficient to achieve such reduction in SCC. According to the teaching of the present invention, the casein-derived peptides are locally administered to the teat-canal of the infected mammary gland, as to restrain the treatment only to the infected gland. The local activity of the peptide on an infected gland permits continuing milking from the other uninfected glands. The milk hygiene is therefore significantly improved immediately after treatment, as the infected gland is typically the only one to contribute to the elevated SCC. The present invention now shows that administration of at least one peptide derived from casein is effective in reducing SCC in sub-clinical infected cows, and to a better extent in clinically infected cows. As the treatment effect can be restricted to the treated gland, an immediate improvement in milk quality is obtained without the need to discard milk from the uninfected gland. This is important, because discarded milk is one of the major causes for economic losses in dairy cows having clinical mastitis (DeGraves and Fetrow, 1993. Vet. Clin. Noth Am. Food Animal Pract. 9:421-434). Administration can be into one mammary gland as well as to all mammary gland, for example to all 4 mammary glands of a lactating cow. Unexpectedly, milk obtained from the treated gland in the next lactating cycle comprises lower somatic cell counts. According to certain embodiments, the casein-derived peptide is administered to a mammary gland or glands of a lactating animal during the dry period, as to increase the milk hygiene in the next lactating period.

The methods of the present invention can be practiced with one type of a peptide derived from casein, or with a plurality of peptide types derived from casein. According to certain embodiments, the methods of the present invention are practiced with the clear, ready to use pharmaceutical compositions of the present invention, described herein below.

According to certain additional embodiments, the peptide derived from casein comprises phosphopeptides. According to additional embodiments, the phosphopeptide comprises an amino acid sequence as set forth in SEQ ID NO:1. According to further embodiments, the phosphopeptide is selected from the group consisting of a phosphopeptide derived from β-casein, a phosphopeptide derived from αS1-casein, and a phosphopeptide derived from αS2-casein. According to certain currently preferred embodiments, the phosphopeptide employed according to the methods of the present invention comprises an amino acid sequence selected from the group consisting of SEQ ID NO:2 to SEQ ID NO:5, and analogs, derivatives and fragments thereof, as these terms are defined herein. The methods of the present invention can be practiced with peptides derived from hydrolysis of casein, as unpurified casein hydrolyzate, purified casein hydrolyzate and peptides purified from the casein hydrolyzate. Additionally, the methods of the present invention can be practiced with synthetic peptides derived from casein. The casein-derived peptides can be incorporated into a pharmaceutical composition.

According to yet another aspect, the present invention provides a method for preventing the suffering associated with mammary gland infection or abrupt cessation of milking in a livestock lactating animal, comprising administering to a mammary gland of the lactating animal a therapeutically effective amount of at least one peptide derived from casein, thereby improving the lactating animal welfare.

According to certain embodiments, improving the lactating animal welfare is measured by the reduction in the number of steps per day and by prolonging the lying period per day of said animal. According to one embodiment, the at least one peptide derived from casein is administered to an infected mammary gland. According to another embodiment, the at least one peptide is administered to a non-infected mammary gland.

The present invention further discloses that unexpectedly, filtration of turbid compositions comprising casein-derived peptides through filters of from 0.1 μm to about 0.5 μm, preferably through filter below 0.25 μm, results in a clear solution, which is highly desirable for pharmaceutical use.

According to further aspect, the present invention provides a pharmaceutical composition comprising a therapeutically effective amount of at least one peptide derived from casein wherein the composition is in the form of a clear, ready to use sterile solution, substantially devoid of micelles, having a pH above 6.0. According to one embodiment, the pharmaceutical composition further comprising a pharmaceutically acceptable diluent, excipient or carrier. According to certain embodiments, the composition comprises a therapeutically effective amount of at least one phosphopeptide derived from casein. According to additional embodiments, the pharmaceutical composition comprises phosphopeptides having an average molecular weight of from about 1,000 to about 5,000 Dalton. According to certain currently preferred embodiments, the average molecular weight of the peptides in the novel pharmaceutical compositions of the present invention is about 2,500 Dalton.

As used herein the phrase "peptides derived from casein" refers to peptides which are cleavage products of casein (referred to herein as peptides derived from natural casein), synthetic peptides, chemically synthesized to correspond to amino acid sequences of the casein units (referred to herein as synthetic peptides derived from casein), and peptides similar (homologous) to casein, for example, peptides characterized by one or more amino acid substitutions, insertions or deletions, such as, but not limited to, permissible substitutions, provided that at least 70%, preferably at least 80%, more preferably at least 90% similarity is maintained, and functional homologues thereof. The terms "homologues" and "functional homologues" as used herein mean peptides with any insertions, deletions and substitutions which do not affect the biological activity of the peptide as described herein.

As used herein, the phrase "combination thereof" is defined as any of the abovementioned peptides, derived from α- or β-casein, combined in a mixture with one or more additional, non-identical peptides derived from α- or β-casein. As used herein, the term "mixture" is defined as a non-covalent combination of peptides existing in variable proportions to one another.

According to certain embodiments, the peptide derived from casein is a phosphopeptide comprising the active motif Ser(p)-Ser(p)-Ser(p)-Glu-Glu (SEQ. ID NO:1). It should be understood that any peptide comprising this motif—whether derived from casein, from a protein other than casein, synthetically synthesized or produced by recombinant technology—which retains the biological activities of the peptides as are described herein, is also encompassed within the scope of the present invention. The phosphopeptides of the present invention are exemplified by peptides having an amino acid sequence as set forth in any one of SEQ ID Nos. 2-5, as listed below:

| SEQ ID NO. | Sequence | Derived from | Residue number |
|---|---|---|---|
| SEQ ID NO: 2 | RELEELNVPGEIVES(P)L S(P)S(P)S(P)EESITR | β-casein | 1-25 |
| SEQ ID NO: 3 | QMEAESIS(P)S(P)S(P) EEIVPDSVEQK | αS1-casein | 59-79 |
| SEQ ID NO: 4 | KNTMEHVS(P)S(P)S(P) EESIISNETYK | αS2-casein | 1-21 |
| SEQ ID NO: 5 | NANEEEYSIGS(P)S(P)S(P) EESAEVATEEVK | αS2-casein | 46-70 |

The present invention also encompasses pharmaceutical compositions comprising analogs, derivatives or fragments of the peptides listed above so long as the analogs, derivatives and fragments retains their biological activity as described herein and the pharmaceutical composition is in the form of a clear solution as defined herein, and the peptide analogs, derivatives and fragments have a molecular weight of from about 1,000 to 5,000 Daltons.

The term "analog" includes any peptide comprising altered sequence by amino acid substitutions, additions, deletions, or chemical modifications of the peptides of the invention and which retain the biological activity of the peptide. By "amino acid substitutions", it is meant that functionally equivalent amino acid residues are substituted for residues within the sequence resulting in a silent change. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are known as conservative substitutions. Additionally, a non-conservative substitution can be made in an amino acid that does not contribute to the biological activity of the peptide. It will be appreciated that the present invention encompasses peptide analogs, wherein at least one amino acid is substituted by another amino acid to produce an active analog of a peptide of the invention having increased stability or longer half-life as compared to the peptide listed herein.

While the amino acid residues of the peptide sequences set forth in SEQ ID NO:1 to 5 are all in the "L" isomeric form, residues in the "D" isomeric form can substitute any L-amino acid residue so long as the peptide analog retains its activity. Methods of producing a retro-inverso D-amino acid peptide analog where the peptide is made with the same amino acids as disclosed, but at least one or more amino acids, including all amino acids are D-amino acids, are well known in the art. When all of the amino acids in the peptide analog are D-amino acids, and the N- and C-terminals of the peptide analog are reversed, the result is an analog having the same structural groups being at the same positions as in the L-amino acid form of the peptide. However, the peptide analog is more stable to proteolytic degradation and is therefore useful in many of the applications recited herein.

The term "derivative" refers to a peptide having an amino acid sequence that comprises the amino acid sequence of the peptide of the invention, in which one or more of the amino acid residues is subjected to chemical derivatizations by a reaction of side chains or functional groups, where such derivatizations do not destroy the activity of the peptide derivative. Chemical derivatization of amino acid residues include, but are not limited to, glycosylation, oxidation, reduction, myristylation, sulfation, acylation, acetylation, ADP-ribosylation, amidation, cyclization, disulfide bond formation, hydroxylation, iodination, and methylation.

The peptide derivatives according to the principles of the present invention also include bond modifications, including, but not limited to, $CH_2$—NH, $CH_2$—S, $CH_2$—S=O, O=C—NH, $CH_2$—O, $CH_2$—$CH_2$, S=C—NH, CH=CH, and CF=CH and backbone modifications. Peptide bonds (—CO—NH—) within the peptide may be substituted, for example, by N-methylated bonds (—N($CH_3$)—CO—); ester bonds (—C(R)H—C—O—O—C(R)—N); ketomethylene bonds (—CO—$CH_2$—); α-aza bonds (—NH—N(R)—CO—), wherein R is any alkyl group, e.g., methyl; carba bonds (—$CH_2$—NH—); hydroxyethylene bonds (—CH(OH)—$CH_2$—); thioamide bonds (—C=S—NH—); olefinic double bonds (—CH=CH—); and peptide derivatives (—N(R)—$CH_2$—CO—), wherein R is the "normal" side chain, naturally presented on the carbon atom. These modifications can occur at any of the bonds along the peptide chain and even at several (2-3) at the same time.

The present invention also encompasses those peptides in which free amino groups have been derivatized to form amine salts, including but not limited to hydrochlorides, p-toluene sulfonyl groups, carbobenzoxy groups, t-butyloxycarbonyl groups, chloroacetyl groups or formyl groups. Free carboxyl groups may be derivatized to form, for example, salts, methyl and ethyl esters or other types of esters or hydrazides. Free hydroxyl groups can be derivatized to form, for example, o-acyl or o-alkyl derivatives. The imidazole nitrogen of histidine can be derivatized to form N-im-benzylhistidine.

Also included as chemical derivatives are those peptides, which contain one or more naturally occurring amino acid derivatives of the twenty standard amino acid residues. For example: 4-hydroxyproline can be substituted for proline; 5-hydroxylysine can be substituted for lysine; 3-methylhistidine can be substituted for histidine; homoserine can be substituted for serine; and ornithine can be substituted for lysine. The peptides can also contain non-natural amino acids. Non-limiting examples of non-natural amino acids are norleucine, ornithine, citrulline, diaminobutyric acid, homoserine, hohocysteine, isopropyl Lys, 3-(2'-naphtyl)-Ala, nicotinyl Lys, amino isobutyric acid, and 3-(3'-pyridyl-Ala). The peptides may also contain non-protein side chains. In addition to the above, the peptides of the present invention can also include one or more non-amino acid monomers or oligomers (e.g., fatty acids, complex carbohydrates, and the like). Also encompassed is any peptide having one or more additions of amino acid residues relative to the sequences of the peptides listed hereinabove, so long as the requisite activity and preferably the molecular weight are maintained. The amino acid residues can be added at the amino terminus and/or carboxy terminus and/or along the peptide sequence.

A peptide derivative according to the present invention can also be a cyclic peptide. Cyclization can be obtained, for example, through amide bond formation, e.g., by incorporating Glu, Asp, Lys, Orn, di-amino butyric (Dab) acid, di-aminopropionic (Dap) acid at various positions in the chain (—CO—NH or —NH—CO bonds). Backbone to backbone cyclization can also be obtained through incorporation of modified amino acids of the formulas H—N(($CH_2$)$_n$—COOH)—C(R)H—COOH or H—N(($CH_2$)$_n$—COOH)—C(R)H—$NH_2$, wherein n=1-4, and further wherein R is any natural or non-natural side chain of an amino acid. Backbone to side-chain and side-chain to side-chain cyclizations are also contemplated.

Cyclization via formation of S—S bonds through incorporation of two Cys residues is also possible. Additional side-chain to side chain cyclization can be obtained via formation of an interaction bond of the formula—(—$CH_2$—)$_n$—S—$CH_2$—C—, wherein n=1 or 2, which is possible, for example, through incorporation of Cys or homoCys and reaction of its free SH group with, e.g., bromoacetylated Lys, Orn, Dab or Dap.

The term "fragment" as used herein refers to a peptide having one or more deletions of amino acid residues relative to the sequences of the peptides listed herein, so long as the requisite activity is maintained. The amino acid residues may be deleted from the amino terminus and/or carboxy terminus and/or along the peptide sequence.

Peptide fragments can be produced by chemical synthesis, recombinant DNA technology, or by subjecting the peptides listed herein to at least one cleaving agent. A cleaving agent can be a chemical cleaving agent, e.g., cyanogen bromide, or an enzyme, e.g., an exoproteinase or endoproteinase. Endoproteinases that can be used to cleave the peptides of the invention include trypsin, chymotrypsin, papain, V8 protease or any other enzyme known in the art to produce proteolytic fragments.

As described hereinabove, the peptides of the present invention can be obtained by hydrolysis of casein, or the peptides can be obtained synthetically.

Hydrolysis of casein is typically performed by digestion with trypsin or pancreatic extracts. Non-digested casein is then separated from the peptide-containing solution, which is further purified from other impurities by a suitable method as is known in the art and as exemplified hereinbelow. According to certain embodiments of the present invention, purification and preparation of the ready-to-use, clear pharmaceutical composition comprises filtration of the solution. According to certain currently preferred embodiments, filtration is performed through 0.2-0.5 μm filter using inert gas including, for example, Nitrogen or Aragon at a low pressure. Preferably, filtration is performed through 0.22 μm filter. Surprisingly, the present invention demonstrates that filtration of a casein hydrolyzate preparation through a membrane with a pore size of below 0.5 μm, preferably at about 0.2 μm, provides a clear solution. The clear appearance of the solution is mainly due to the removal of remaining undigested casein micelles. Casein micelle forming colloidal particles provide for the non-transparent, white color of milk. It should be understood that pharmaceutical compositions having the same characteristics of the pharmaceutical composition of the present invention, i.e. comprising a therapeutically effective amount of at least one peptide derived from casein, being in the form of a clear solution substantially devoid of micelles, wherein the at least one peptide has a molecular weight in the range of 1,000-5,000 Dalton, obtained by other methods as are known in the art, are also contemplated within the scope of the present invention.

The pharmaceutical compositions of the present invention are very stable. As used herein, the term "stable" refers to the activity of a peptide derived from casein after incubation at a certain temperature, which retains at least 85%, preferably 90%, more preferably 95% or more of the initial peptide activity.

The phosphopeptides within the pharmaceutical compositions of the invention are stable in high as well as in low temperatures. The phosphopeptides within the pharmaceutical composition can be kept frozen without substantial loss of activity. In addition, the pharmaceutical composition can be heated to up to 70° C. for about 15 min without loss of activity.

The present invention provides pharmaceutical composition comprising peptides derived from casein, which is in the form of a ready to use, clear, sterile solution. This composition is advantageous to the currently available casein-derived products, as the clarity of the solution enables an easy, fast detection of any contamination, specifically microbial contamination. The ready to use solution requires no reconstitution steps prior to administration, compared to many hitherto known compositions provided in the form of a powder. According to certain embodiments the pharmaceutical compositions of the present invention are intended for veterinary use, such that the pharmaceutical composition should be administered to a large number of subjects. The pharmaceutical compositions of the present invention meet with the needs of such conditions, providing an easy detection of contamination and a ready to use formulation.

The clarity of the solution can be measured by any methods known to a person skilled in the art. According to certain embodiments, the clarity of the solution is determined according to its turbidity value. As used herein, a "clear" solution is a solution having a turbidity value of less than 6 NTU.

The term "pharmaceutical composition" is intended in a broader sense herein to include preparations containing a protein composition in accordance with the present invention used not only for therapeutic purposes, but also as reagents or diagnostic purposes as known in the art. The pharmaceutical composition intended for therapeutic use should contain a therapeutic amount of a peptide derived from casein, i.e., that amount necessary for preventative or curative health measures. If the pharmaceutical composition is to be employed as a reagent or diagnostic, then it should contain reagent or diagnostic amounts of the peptide derived from casein.

According to certain embodiments, the protein concentration of the pharmaceutical composition of the present invention is from about 10 ng/ml to about 15 mg/ml.

The term "pharmaceutical composition" further refers to a preparation of one or more of the peptides described herein, with other chemical components such as pharmaceutically suitable diluents, carriers and excipients. The purpose of a pharmaceutical composition is to facilitate administration of a compound to an organism.

The term "pharmaceutically acceptable carrier" as used herein, refers to a carrier or a diluent that does not cause significant irritation to an organism and does not abrogate the biological activity and properties of the administered compound. Non-limiting examples of carriers are: water, propylene glycol, saline, emulsions and mixtures of organic solvents with water. The term "excipient" as used herein refers to an inert substance added to a pharmaceutical composition to further facilitate administration of a compound. Non-limiting examples of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, the contents of which are incorporated by reference herein. According to certain currently preferred embodiments, the pharmaceutical compositions of the present invention are formulated for parenteral administration, e.g. for intracanal administration, particularly for injection or infusion into the teat canal of a mammary gland. For injection, the peptides of the invention can be formulated in aqueous solutions, preferably in physiologically compatible buffers such as Hank's solution, Ringer's solution, or in physiological saline buffer with or without organic solvents such as propylene glycol and polyethylene glycol. Intracanal administration to a teat canal of a mammary gland is not defined in terms of topical or systemic administration. As disclosed herein, intracanal administration of the pharmaceutical composition of the invention can have a local effect, for example by inducing involution only in the treated mammary gland, and may therefore be referred to as topical administration. The pharmaceutical compositions may be also administered topically as a gel, ointment, cream, emulsion or sustained release formulation including a transdermal patch. The present invention further encompasses systemic administration, either perenterally or orally.

According to another aspect, the present invention provides a pharmaceutical composition comprising a therapeutically effective amount of at least one peptide derived from casein in the form of a lyophilized powder, wherein the powder is reconstituted to a liquid before use to form a clear solution, substantially devoid of micelles and having a pH above 6.0.

According to a further aspect, the present invention provides a pharmaceutical composition comprising a therapeutically effective amount of at least one peptide derived from casein wherein the composition is in the form of a clear, ready to use sterile solution, substantially devoid of micelles, having a pH above 6.0, for treating a mammary gland of a lactating animal, including inducing transient cessation of milk production and inducing persistent cessation of milk production.

According to yet further aspect, the novel pharmaceutical composition of the present invention is useful for the prevention and treatment of infection or reversal of infection. According to additional embodiments, the pharmaceutical composition comprises phosphopeptides having an average molecular weight of from about 1,000 to about 5,000 Dalton. According to certain currently preferred embodiments, the average molecular weight of the peptides is about 2,500 Dalton.

According to certain embodiments, the lactating animal is selected from the group of animals consisting of humans, cows, goats, sheep, buffalos, camels, donkeys, llamas, horses, pigs, cats and dogs.

According to certain currently preferred embodiments, the lactating animal is a human. In the last few decades, breast-feeding has declined in all the technologically advanced societies of the world and also, even to a lesser extent, in developing countries. Many women choose not to nurse their babies at all or cease nursing after a short period of time. Others are prevented from nursing due to various medical reasons, including women suffering from certain transmissible or non-transmissible diseases, a specific example being women carrying HIV. Current recommendation of health authorities to HIV carriers is to maintain breast-feeding for only about 10 weeks after delivery, after which only milk substitutes should be provided. Women that gave birth to premature babies, or term babies that did not survive are also prevented from nursing. In all such events, milk is produced by the mammary gland but is not milked. Such milk stasis is associated with swelling of the breast to an extent that may cause conspicuous agony, both physically in psychology. In addition, milk stasis is frequently associates with leaking of the mammary secretion, which subsequently increases the risk of acquiring intramammary infection. The pharmaceutical compositions and methods of the present invention thus answer the need for a rapid and efficient induction of involution and cessation of milk production as to prevent the above-described undesirable conditions.

According to additional currently preferred embodiments, the animal is a livestock animal selected from the group consisting of cow, buffalo, goat and sheep.

The novel pharmaceutical compositions of the present invention are effective for inducing transient or persistent milk cessation. Transient effect on milk yield can be obtained in a mammary gland of a lactating animal in response to a single application, typically by direct injection or infusion into the gland cistern through the teat canal of the pharmaceutical composition of the invention. Typically, single injection or infusion causes a sharp decline in milk production after about 8 hours. The present invention now discloses that a single administration of the pharmaceutical compositions of the present invention can also cause persistent milk cessation and involution. Cessation of milk production occurs only in the treated gland; this phenomenon is of a significant importance, as milking from untreated glands can continue as to limit the loss of milk yield. Alternatively, if so desired, all mammary glands of a lactating animal can be treated as to induce cessation of milk production.

The involution process induced by the pharmaceutical compositions of the present invention is more rapid and synchronized compared to involution induced by cessation of milking, and milk production can be resumed by mechanical stimuli like milking. Resumption of milk production also occurs, as in the natural process of involution, after a subsequent pregnancy and parturition. The rapid involution induced by the compositions of the present invention does not interfere with re-building of the mammary gland tissue and restoration of milk secretion capacity towards parturition.

The novel pharmaceutical compositions of the present invention are further useful for the treatment of an infection of the mammary gland. As used herein, the term "treatment" refers to the prevention of infection as well as to the treatment of an infected gland as to reverse the infection and heal the mammary gland, both in human and non-human mammals.

The pharmaceutical compositions of the present invention are useful in the treatment of a wide range of microbial infections, including infections caused by gram-positive bacteria, gram-negative bacteria, fungi, mycoplasma and viruses.

According to certain embodiments, the pharmaceutical compositions are useful in treating mastitis, specifically in livestock animals including cows, sheep, buffalos and goats.

Clinical and subclinical mastitis are inflammatory states of the udder resulting mainly from bacterial infection. Mastitis has a variety of bacterial etiologies and causes great losses in milk production annually. Pathogenic microorganisms that most frequently cause mastitis can be divided into two groups based on their source: environmental pathogens and contagious pathogens. The major contagious pathogens are *Streptococcus agalactiae, Staphylococcus aureus*, Coagulase-negative *staphylococcus* (CNS) and *E. Coli*. With the exception of some mycoplasmal infections that may originate in other body sites and spread systemically, these five major types of microorganisms gain entrance into the mammary gland through the teat canal. Contagious organisms are well adapted to survival and growth in the mammary gland and frequently cause infections lasting weeks, months or years. The infected gland is the main source of these organisms in a dairy herd and transmission of contagious pathogens to uninfected quarters and cows occurs mainly during milking time.

Clinical mastitis is easily diagnosed due to marked alterations in milk composition and appearance, decreased milk production, elevated body temperature and swelling, redness, or fever in the infected glands. Subclinical mastitis, the most prevalent form of the disease, often remains undetected because signs are not readily apparent. Many subclinical IMI tend to persist, resulting in a decrease of milk quality due to elevated milk SCC, and also due to a decrease in milk production. IMI localized in a single mammary gland may lead to the development of clinical mastitis and to the spread of certain mastitis pathogens from infected mammary quarters to uninfected ones. In contrast to clinical mastitis, it is not usually advisable to treat livestock animals having subclinical mastitis by antibiotic administration during lactation (Gruet et al., 2001. Adv. Drug Delivery Rev. 50:245-259) because the cure rate is low and because the cost of the treatment and a withdrawal period of 4-5 days of milk make it economically unjustified (Yamagata et al., 1987. J. Am. Vet. Med. Assoc. 191:1556-1561). The pharmaceutical compositions of the present invention can be administered during the lactating period. As described herein, the compositions of the invention can have a local effect, such that the treatment can be administered only to the infected mammary gland(s), while milking from the uninfected gland(s) can continue, reducing the milk loss to a minimum.

For treating mastitis, administration of repeated doses of the pharmaceutical compositions of the invention into the infected mammary gland may be required. Typically, administration is repeated at least once, preferably between 1-10 times, more preferably 1 to 3 times, at an interval selected from the group consisting of about 6 hours, about 8 hours, about 12 hours, about 16 hours, about 20 hours and about 24 hours during 1 to 10 days, preferably 1 to 3 days.

According to certain embodiments, the novel pharmaceutical compositions of the present invention are administered for the treatment of udder infections during the dry period. The treatment can either be directed at treating infected glands (dry cow therapy) or as a prophylactic therapy (dry cow preventive therapy). Treatment of infections at the onset and during the dry period is advantageous over treatment during lactation as it enables administering the pharmaceutical composition not only to an infected gland having visible infection signs but to all glands of the udder. Such administration results in eradication of existing infection, and prevents acquiring new infections during the dry period. Moreover, the present invention demonstrates that administering the pharmaceutical compositions of the invention during the dry period dramatically decrease the infection incidence in the subsequent lactating period. The pharmaceutical compositions can be administered to a mammary gland identified as having clinical or subclinical mastitis, to a non-infected gland as prophylactic treatment, or to both.

According to additional embodiments, the novel pharmaceutical composition of the present invention is administered in combination with an additional anti-microbial treatment selected from the group consisting of, but not limited to, antibiotic, bactericide, steroidal and non-steroidal anti-inflammatory treatment, treatment with an immunomodulator and vaccination. According to one embodiment, the pharmaceutical composition of the present invention and the additional anti-microbial treatment are co-administered, either as a combined, single pharmaceutical composition or as separate compositions. Alternatively, the pharmaceutical composition of the present invention is administered as a pre-treatment followed by the application of the additional antimicrobial treatment, and vise-versa.

The following examples are presented in order to more fully illustrate the preferred embodiments of the invention. They should in no way be construed, however, as limiting the broad scope of the invention.

EXAMPLES

Example 1

Preparation of Pharmaceutical Composition

Commercial bovine casein (e.g. Sigma) was dissolved (100 g/liter) in 25 mM Tris-buffer, pH 8 and digested with trypsin (500 U/liter) for 4 h at 37° C. The solution was then acidified to pH 4.7 with HCl, and the non-digested casein was pelleted by centrifugation. The supernatant was boiled for 15 min, cooled to room temperature, and adjusted to pH 7 with NaOH solution. Material that had not dissolved under these conditions was removed by centrifugation and discarded. Alternatively, a food grade commercial casein hydrolyzate was used as a starting material, and 1-40 g/liter were dissolved in saline or water yielding pH of approximately 7.2. The water and saline used throughout the process complies with USP monographs for "Water for Injection". The solution was then heated to 40-60° C. and, after cooling, filtered through 5 micron filters using inert gas such as nitrogen or argon at low pressure (1-6 psi). Several batches required an additional filtration through 3 micron filters. The filtrate was then heated to 50° C. to 70° C. as to increase the solubility of the peptides.

The resulting turbid solution was then filtered through a 0.2 micron filter using inert gas such as nitrogen or argon at low pressure (1-6 psi). This filtration step removed all the remaining casein micelles, such that the solution obtained after the filtration was clear. The filtrate was sampled and assayed for total peptide content by the Bradford method, and the protein concentration was adjusted to 5-15 mg/ml. The pH of the solution was then adjusted with either concentrated HCl (reagent grade ACS) or 1.0 normal NaOH to about 7.3-7.6, and the solution was filtered again through 0.2 micron filters with inert gas at low pressure. The final filtrate (about 10 ml) was then filled and sealed into 20 ml sterilized glass ampoules while in an inert gas atmosphere.

With certain commercial casein hydrolyzate sources a pre-filtration step through 5 micron filter using inert gas such as nitrogen or argon at low pressure (1-6 psi) may be required in order to prevent plugging of the 0.2 micron filter at the end of the process.

The clarity of the solution was determined by turbidimeter (Micro 100 General Purpose Turbodometer, Metex Cooperation, Toronto, Canada). The obtained solution was clear, having an NTU of 4.0. The resulted composition is designated herein as MLTS-2.

Example 2

Treatment of Mastitis

Example 2.1

Dry Therapy Applied to Cows having Mastitis

Cow Population

Thirty-two cows participated in the study (8 cases, i.e. cows receiving a treatment, vs. 24 controls, chosen according to the study design, see below). The eight case cows diagnosed to have clinical and/or subclinical mastitis according to bacteriological diagnosis were enrolled to receive treatment with the composition of the invention prepared as described in example 1 above (MLTS-2). 24 cows served as a control, of which 6 were diagnosed to have mastitis as above and 18 were not infected. Clinical mastitis is characterized with visible signs including flakes or clots in the milk, sharp increase in SCC, fever, rapid pulse, loss of appetite, dehydration and depression. Infected quarter or the udder may also be swollen. Subclinical mastitis is characterized by milk production decline, reduced milk quality and elevated SCC that is detected by an increase in the bulk tank somatic cell count. Control and assayed cows were sampled from the same herd and were of same race.

Inclusion criteria for all cows were: late stage of lactation, 1-2 weeks prior to the expected first day of the dry period; four functional quarters; pregnant; no significant external teat lesion; cows that did not receive systemic anti-mastitis therapy 4 weeks before enrolment; cows that did not consume food with antibiotic 4 weeks before enrolment; no signs of morbidity which may have potential influence on the outcome of the treatment according to the judgment of the investigator. Mastitis diagnosed cows were cows with confirmed IMI and SCC of at least 400,000 cells/ml.

Cows were excluded from the study according to the following exclusion criteria: cows receiving immunotherapy 4 weeks before enrolment; cows receiving antibiotic, hormone, anti-inflammatory and/or anabolic therapies, either systemic or by feeding 4 weeks before enrolment; cows receiving vaccines therapy 12 months before enrolment; concurrent use of immuno- and vaccine therapies, either systemic or by feeding; concurrent other alternative therapies; cows with active tuberculosis or other infectious diseases according to the judgment of the investigator; concurrent use of anabolic steroids, either systemic or by feeding; concurrent use of hormones, either systemic or by feeding.

Study Design

Treated (case) and control cows were selected as to minimize external variance, by defining a match score according to the following variables: herd, race, number of calves, date of calve, number of drying periods, date of drying, and cow date of birth. Full match was scored as 5; no match was scored as 0. A full match was required for herd and race. Additional factors include (from the most to the less important factor): number of parturitions (allowed match ±1), difference of parturition date (allowed match ±2 months), number of dry periods (allowed match ±1), difference of dry period beginning date (allowed match ±2 months), date of birth (allowed match ±3 months).

Cows were enrolled to the study one or two weeks before the scheduled entrance into the dry period, which is about 75 days before parturition. Within this period, the following parameters were measured as to set a baseline data: general udder appearance; SCC; existence of IMI according to bacteriologic test and visible signs. About 60 days before parturition, milking was stopped and treatment was administered. Assay cows received 10 ml of MLTS-2 with 8 mg/ml peptide twice a day during 3 days. Control cows diagnosed to have mastitis received dry-cow treatment of a broad range antibiotic (Cefquinome, 75 mg per application). Administration was by injection into a gland cistern through the teat canal of the mammary gland as a single dose to each quarter. All four quarters of an udder were treated. For each injected dose a new vial was used. Used vials were kept for verification of compliance and accountability by the monitor of the study. After the last treatment the cows were not milked any more until the next lactation period after parturition. Following completion of the 3 days treatment, cows were followed for about 9 weeks during the dry period for visible signs of mastitis. The presence of microorganisms in each quarter of the udder by bacteriological test, general udder appearance and SCC were examined during the next lactating period one, two and three months after parturition.

Results

Table 1 below shows that none of the microorganisms detected before treatment were present after the treatment (i.e., the cure rate of existing infection was 100%).

TABLE 1

Effect of dry period treatments on bacterial cure and new infections in cows treated with casein hydrolyzate (8 cows, 32 quarters) in comparison to the matched control cows (24 cows, 96 quarters)

|  | Microorganism detected before treatment (No. of Quarters) | | Same microorganism detected in the next lactation (0-89 days post calving) (No. of Quarters) | |
|---|---|---|---|---|
|  | Cases | Controls | Cases | Controls |
| S. aureus | 3 | 5 | 0 | 2 |
| S. dysgalactia | 4 | 7 | 0 | 4 |
| S. chromoge | 0 | 5 | 0 | 2 |
| S. uberis | 1 | 4 | 0 | 2 |
| E. coli | 1 | 6 | 0 | 3 |
| CNS | 2 | 4 | 0 | 0 |
| Others | 0 | 3 | 0 | 5 |
| Infected quarters | 11 | 34 | 0 | 18 |
| Cure rate (%) | — | — | 100% | 47.1% |

Note:
S denotes *Staphylococcus*;
CNS denotes coagulase negative *streptococcus*

Control cows that were not diagnosed to have mastitis at the beginning of the study, and did not receive any treatment, developed mastitis during this period (n=12 quarters out of 18 quarters); other 6 quarters recurrent infection, one by the same microorganism and the rest 5 quarters by microorganism of different type.

Example 2.2

One Dose Dry Therapy Applied to Cows at the Herd Level Comprising With or Without Mastitis Study Design The aim of this experiment was to study the effectiveness of MLTS-2 as a dry cow therapy at the herd level. Fifty-five Holstein cows from one dairy herd being at least at the second lactating period, participated in the experiment from Jul. 25, 2005 to Nov. 11, 2005.

The study was performed according to the Guidelines of the International Coordination of Harmonization in Veterinary. Inclusion and exclusion criteria were as described in Example 2.1.

Cows were enrolled to the study one or two weeks before the scheduled entrance into the dry period, which is about 75 days before parturition. Milk samples were aseptically collected and cultured in accordance with established guidelines from each quarter at least two times before the scheduled time of dry-off treatment. Pre-dry off intramammary infection (IMI) was defined by identification of at least two positive cultures. Within the pre-treatment period, the following parameters were measured as to set a baseline data: general udder appearance; SCC; existence of IMI according to bacteriologic test and visible signs. About 60 days before parturition, milking was stopped and treatment was administered. Treatments were administrated aseptically by intramammary infusion into four quarters of the fifty-five assay cows. Each quarter was infused once with 10 ml of MLTS-2 containing 8 mg peptide per ml. For each injected dose a new vial was used. Used vials were kept for verification of compliance and accountability by the monitor of the study. After the last treatment the cows were not milked any more until the next lactation period after parturition. Following completion of the treatment, cows were followed for about 9 weeks during the dry period for visible signs of mastitis. To assess cure rate and new infection rate at the quarter level, foremilk samples from all quarter were taken for the first two months of the subsequent lactation and cultured on appropriate media. Quarters with two consecutive negative milk cultures were presumed to have a microbiologic cure or non-infected quarter. One and two months after parturition, general udder appearance and SCC were examined. All parameters were compiled for each quarter and analyzed by SAS/STAT package for before vs. after effects using the chi-squared test.

Results

At the initial sampling, 14 cows (25.5%) were found to have an infection, of which 19 quarters (8.6%) were infected. The predominant organisms detected were *staphylococcus* variants (14/19) (Table 2).

TABLE 2

IMI detected before and after treatment (cows n = 55, quarters n = 220)

| Before treatment | | IMI in treated cows after calving (Samples examined for same bacteria as before treatment) | | | |
|---|---|---|---|---|---|
|  |  | IMI | | Non-IMI | |
| Cows | Quarters | Cow | Quarter | Cows | Quarters |
| 14 | 19 |  | 1 | 1 | 13 | 18 |
| %: 14/55 | 19/220 | Prev.: 1/14 | 1/19 | Cure: 13/14 | 18/19 |
| Detected Bacteria: | | | Detected Bacteria | | |
| S. epidermidis, n = 2 | | | S. chromogens | | |
| S. chromogens, n = 7 | | | | | |
| CNS, n = 2 | | | | | |
| S. aureus, n = 2 | | | | | |
| S. xyosos, n = 1 | | | | | |
| Strep NOS, n = 1 | | | | | |
| Strep. dysgalactiea, n = 3 | | | | | |
| Strep. Uberis, n = 1 | | | | | |

Note:
S. denotes *Staphylococcus*;
CNS coagulase negative *Staphylococci*;
NOS not otherwise specified.
Strep, *streptococcus*.
Prev. denotes prevalence.
Difference in the existence of IMI between before and after treatment was statistically significant, $p < 0.005$.

The data show that after calving only one quarter remained infected with the same type of organism up to 89 days.

Example 2.3

Treatment of Mastitis During Lactation

Thirty-seven cows were enrolled to this study. All cows were diagnosed to have clinical mastitis in one gland. Casein hydrolyzate was administered by injection into the infected gland cistern through the teat canal of the mammary gland twice a day: once during the morning and once during the afternoon.

The cows that participated in the study were at a different stages regarding number of parturition, and, accordingly, number of lactation. Organisms were identified and quantified by standard laboratory techniques (Leitner et al., 2004 Dairy Sci. 87:46-52). Positive finding were based on two consecutive identification of known mastitis pathogens. As is evident from Table 3 below, the pharmaceutical composition of the present invention is highly effective in treating mastitis during the lactation period.

TABLE 3

Effect of MLTS-2 on bacterial cure in cows having IMI during lactation

| Pathogens | Number of glands infected with microorganism before treatment | Number of glands infected with microorganism after treatment |
|---|---|---|
| S. aureus | 5 | 1 |
| All streptococci | 6 | 2 |
| E. coli | 4 | 1 |
| A. pyogenes | 10 | 0 |
| Others | 8 | 0 |
| Total Cure rate (%) | 33 | 4 |

Example 3

Shortening the Dry Period

Cow Population

Cows are enrolled to the study according to the inclusion/exclusion criteria described in Example 2.1 above. Match score between a treated (n=5) and a control group (n=15) is also as in the aforementioned example. Within the control group, at least one fifth of the cows are diagnosed to have mastitis and are treated with antibiotic dry cow therapy.

Study Design

Cows are enrolled to the study two weeks before the scheduled entrance into the study. Entrance into the study took place about 60, 40, 30, 20 and 10 days before anticipated parturition. Before entrance to the study, the following parameters were measured as to set a baseline data: SCC; existence of IMI according to bacteriologic test and visible signs, and milk yield. Casein hydrolyzate, prepared as described in Example 4 hereinbelow, was administered only once a day. Reducing the number of administrations to a single application is highly desirable, as a single-treatment simplify considerably the procedures and the workload in a given farm, hence, the likelihood that farmers will adopt the procedure.

Administration was by injection into a gland cistern through the teat canal of the mammary gland. For each injected dose a new vial was used. Used vials were kept for verification of compliance and accountability by the monitor. After the treatment the cows were not milked any more until the next lactation. Following completion of the treatment, cows were followed (including udder examination) during the dry period imposed. In addition, after parturition, the following parameters were examined: SCC; IMI by bacteriologic test and visible signs, and assessment of the teat canal including assessment of open or close canal and plug consistency. Milk yield was also measured. A treatment is defined as successful when it causes complete cessation of milk production, and does not have any adverse effect on the parameters measured after parturition. Shortening the dry period to 45 days or less is defined as highly successful. Statistic analyzes were as described in Example 2.2 hereinabove. As is known, milk yields increase from the first lactation period (after first parturition) to at least the fourth lactation period. Therefore, in order to standardize the milk yield of treated vs. not treated cows, milk yield data were corrected according to the lactation number as follows: for first lactation, milk liter per day was divided by 0.795; for the second lactation milk liter per day was divided by 0.965; for the third lactation, milk liter per day was divided by 1.001, and for the fourth and more—no standardization was performed. These correction factors are currently used by the Israeli Cow Breeding Association (ICBA) for genetic selection of cows in Israel.

Results

All cases and control cows calved according to the study design, and no case of abortion or any other postpartum disease was recorded. The length of the dry period (in days) in the preceding lactation was the same for cases and controls. On the other hand, in the current lactation the length of the dry period was significantly shorter (p <0.01) in cases compared to controls after treatment with casein hydrolyzate (Table 4).

TABLE 4

Effect of treatment with casein hydrolyzate on the length of the dry period

| | Dry period after previous lactation | | Dry period after current lactation | |
|---|---|---|---|---|
| | Cases | Controls | Cases | Controls |
| Length (day) | 60.8 | 63.9 | 39.2 | 62.1 |
| Range | 55.69 | 60.70 | 31.45 | 55.71 |

After calving, milk yield after calving did not differ between cows in which the dry period was shortened at least during the time periods describe in Table 5 hereinbelow.

TABLE 5

Milk yield after treatment with casein hydrolyzate applied to shorten the dry period

| | Previous lactation period | | | Current lactation period | | |
|---|---|---|---|---|---|---|
| Days of lactation | Average milk yield per day (liters) | | Difference between cases and controls | Average milk yield per day (liters) | | Difference between cases and controls |
| 4-33 | 40.7 | 41.6 | 0.98 | 43.9 | 45.6 | 1.69 |
| 34-63 | 43.4 | 46.4 | 3.01 | 49.8 | 50.7 | 0.89 |
| 64-104 | 43.7 | 47.2 | 3.50 | 49.8 | 51.5 | 1.82 |

Example 4

Reduction of Milk Somatic Cell Counts

Example 4.1

Somatic Cell Count in Lactating Cows Treated with Casein Hydrolyzate Over Three Days Cow Population Thirty-seven cows completed the study, after an initial recruitment of 42. Cows were eligible for recruitment in this study if they had four functional quarters, of which at least one was infected, had no significant teat lesion, were in good health and had not received antibiotic and/or anti-inflammatory therapy within 30 days before the beginning of the treatment. In addition, no mastitis vaccines were used in any of the herds from which the cows were selected at least during the previous year. The cows in these farms were fed a typical Israeli total mixed ration that comprised 65% concentrates and 35% forage containing 17% of protein.

Preparation of Casein Phosphopeptides

Casein hydrolyzate, comprising casein phosphopeptides was prepared as previously described (Shamay et al., 2003, supra). The procedure took place in Hy Laboratories (Rehovot, Israel), ensuring that the final product was sterile and that the product was bottled in sterile vials. Endotoxin level in the final product was 0.48 EU/ml according to the Limulus Amebocyte Lysate (LAL) test. The amount of endotoxin injected with 10 ml of this solution, 0.0001 EU/kg body weight (assuming average cow body weight of 500 kg), is 2000 times lower than the tolerance limit of endotoxin in intrathecal administrated human drugs (K=tolerance limit in EU/kg=5 EU/kg for parenteral drugs and 0.2 EU/kg for intrathecal drugs). The final products for single injection into a single quarter contained 10 ml CNH with peptide concentration of 10 mg/ml.

Study Design and Results

Casein hydrolyzate was administered twice a day during three (3) days to the only infected mammary gland of the udder through the teat canal. Milking and induction of the dry period were continued according to the regular schedule of the herd.

Milk samples were examined at the Israeli Cow Breeding Association (ICBA) central laboratory, Caesarea, Israel or at the National Mastitis Reference Center, Kimron Veterinary Institute. Organisms were identified and quantified by standard laboratory techniques (Leitner et al., 2004. Dairy Sci. 87:46-52). Positive finding were based on two consecutive identification of known mastitis pathogens.

Somatic cell counts in the milk before applying the treatment (SCC-PRE) were compared to the SCC observed after calving (SCC-POST). SCC-PRE presented in Table 6 hereinbelow is the average of two measurements up to 15 days before the application of casein-hydrolyzate treatment. Presented SCC-POST is the average of at least two measurements between 15-60 days after calving. For 27 cows, SCC was also followed once monthly for up to 10 months after parturition.

Statistical Analysis

SCC-PRE was compared to SCC-POST with the SAS/STAT package by using the chi-square test for SCC and the one-way ANOVA for continuous variables. All milk samples were analyzed for SCC with a Fossomatic 360 at the ICBA laboratory and converter the log scale for statistic analysis.

Results

Data were collected from 37 cows from 9 herds (2 to 7 cows/herd) with a confirmed diagnosis of mastitis in one quarter. The most prevalent identified pathogens were *Arcanobacterium pyogenes*, *Staphylococcus aureus*, *Escherichia Coli* and *Streptococcus uberis*. Infection with *Streptococcus* species, *P. auroginosa*, *Corynobacteruim bovis* and *Micrococcus* were exclusively sub-clinical, whereas ~60% of infections with *S. aureus*, *E. Coli* and *A. pyogenes* were clinical and ~40% subclinical.

There were significant differences between SCC-PRE (average 2,210,200) and SCC-POST (average 205,000) either when tested for individual pathogen or in the whole study group (p<0.001) (Table 6).

TABLE 6

Effect of casein hydrolyzate on post-calving SCC in lactating cows treated in one infected glands.

| | | Somatic Cell Counts | |
|---|---|---|---|
| Pathogens | Number | SCC-PRE Average | SCC-POST Average |
| *Staphylococcus aureus* | 5 | 1,235.2 | 147.4 |
| All *Streptococcus* | 7 | 3,357.4 | 262.3 |
| *Escherichia Coli* | 5 | 1,781.2 | 275.4 |
| *Arcanobacterium pyogenes* | 10 | 1,465.1 | 145.6 |
| Others All | 6 | 3,283.5 | 226.7 |
| Average SCC | | 2,210.2 | 205.0 |
| Standard deviation | | 2,374.3 | 170.2 |

In the clinically infected glands, SCC-POST in 75% of the cows (n=9/12) was 201,000 cells/ml or less after treatment, and in all the treated cows SCC-POST was 401,000 cells/ml or less (Table 7). In the subclinical infected glands, SCC-POST in 57% (n=12/21) of the cows was 201,000 cells/ml or less after treatment and in 81% of the cases 401,000 cells/ml or less. When considering all the data set, SCC-POST in 63.6% (n=21/33) of the cases was below 201,000 cells/ml, which was significantly higher (p<0.01) than the number of cases (n=12/33) in which SCC-POST was above 201,000 cells/ml.

TABLE 7

Effect of casein hydrolyzate on post-calving SCC in lactating cows treated in single infected glands.

| Mastitis Stage | SCC After Treatment | | |
|---|---|---|---|
| before treatment | 0-200 | 201-400 | >401 |
| Clinical | 9 cows | 3 cows | 0 cows |
| Subclinical | 12 cows | 5 cows | 4 cows |
| Average SCC | 95.6 | 329.4 | 530.9 |
| Standard deviation | 45.8 | 67.1 | 133.4 |

For 27 cows, on average, 6.1 months elapsed between treatments and induction of drying, i.e. the calving was after the dry period. Thus, in these cows, SCC-POST represents the SCC observed in the a lactation period after a dry period. In 59.3% of the cows (16/27), SCC-POST was below 201,000 cells/ml, which is not significantly different from 21/23, the number of cases in which SCC-POST was below 201,000 cells/ml in the period between treatment and dry-off. It is worth noting that in almost 26% of the cows SCC-POST was below 101,000 cells/ml during the whole follow-up observation and in 85% (23/27) SCC-POST was less than 401,000 cells/ml.

Example 4.2

Effect of One Dose of Casein Hydrolyzate Administered to Four Gland on Post-calving Somatic Cell Count Reducing the number of treatments to a single one is very important from a practical point of view because a single-treatment should simplify considerably the procedures and the workload in a given farm, hence, the likelihood that farmers will adopt this procedure.

The aim of this experiment was to study the effect of casein hydrolyzate treatment applied at a one dose to four glands on post-calving somatic cell count. Holstein cows (55), being at least at the second lactating period, from one dairy herd participated in the experiment from July 25th to Nov. 11, 2005.

Study cows, inclusion and exclusion criteria, milk sampling, and study protocols are essentially as described in Example 2.1 hereinabove. Somatic cell counts in the milk before applying the treatment (SCC-PRE) were compared to SCC observed after calving (SCC-POST). SCC-PRE was the average of two measurements up to 15 days before the treatment in each individual gland. SCC-POST was the average of at least two measurements between 15-60 days (interval 15-30, 31-60) after calving date. Data and SCC were analyzed as in Example 4.1.

Results

Before treatment, the average SCC-PRE measured in infected quarters (19 quarters of 13 cows) was 557,278 cells/ml compared to 183,381 cell/ml (p<0.001) in non-IMI quarters. As shown in Table 8 below, the treatment was effective in reducing the SCC-POST (p<0.01). The difference between SCC before and after the treatment was more notable in intramammary infected glands (p<0.001) in comparison to the difference for non IMI glands (p<0.05); however, these results clearly demonstrates that application of casein derived peptides reduces the SCC in milk, and thus improving the milk hygiene when applied to an infected as well as to non-infected glands.

TABLE 8

Effect of casein hydrolyzate on post-calving SCC in infected and non-infected glands

| | SCC-PRE (Cells/ml) | SCC-POST (Cells/ml) | | |
| --- | --- | --- | --- | --- |
| | | 15-30 days | 31-60 days | Average |
| Infected-IMI | 557,278* | 146,851* | 154,301* | 149,201* |
| Non Infected/IMI | 183,381*** | 160,945*** | 175,813 | 167,232*** |
| All | 214,777** | 156,480** | 169,230** | 164,914** |

*p < 0.00.1;
**p < 0.01;
***p < 0.05

Example 5

Effect of Casein Hydrolyzate on Milk Yield After Parturition

Example 5.1

Effect of Multiple Applications of Casein Hydrolyzate

Cow Population

Eleven cows (cases) diagnosed to have clinical and/or subclinical mastitis by bacteriological diagnosis were enrolled to receive treatment with casein hydrolyzate. 33 cows served as a control, of which 6 were diagnosed to have mastitis as above and 27 were not infected. Control and assayed cows were sampled from the same herd and were of same race.

About 60 days before parturition, milking was stopped and treatment was administered. Assay cows received 10 ml of MLTS-2 with 8 mg/ml peptide twice a day during 3 days. Control cows received antibiotic dry-cow treatment as a single treatment. All four quarters of an udder were treated. Cows were not milked between treatments; residual milk accumulation was discarded from the treated gland before casein hydrolyzate treatment.

Data from this trial was subjected to three-way ANOVA with a repeated-measurements ("split-plot") design using Groups (treated cows vs. control cows); lactation (lactation tested: 1, 2, 3, or 4-5) and month after parturition (1st, 2nd, 3rd or 4th month in lactation). For the comparison of the average milk production before and after the treatment milk yield per day was standardized as described in Example 3 hereinabove.

Results

Figure 2:
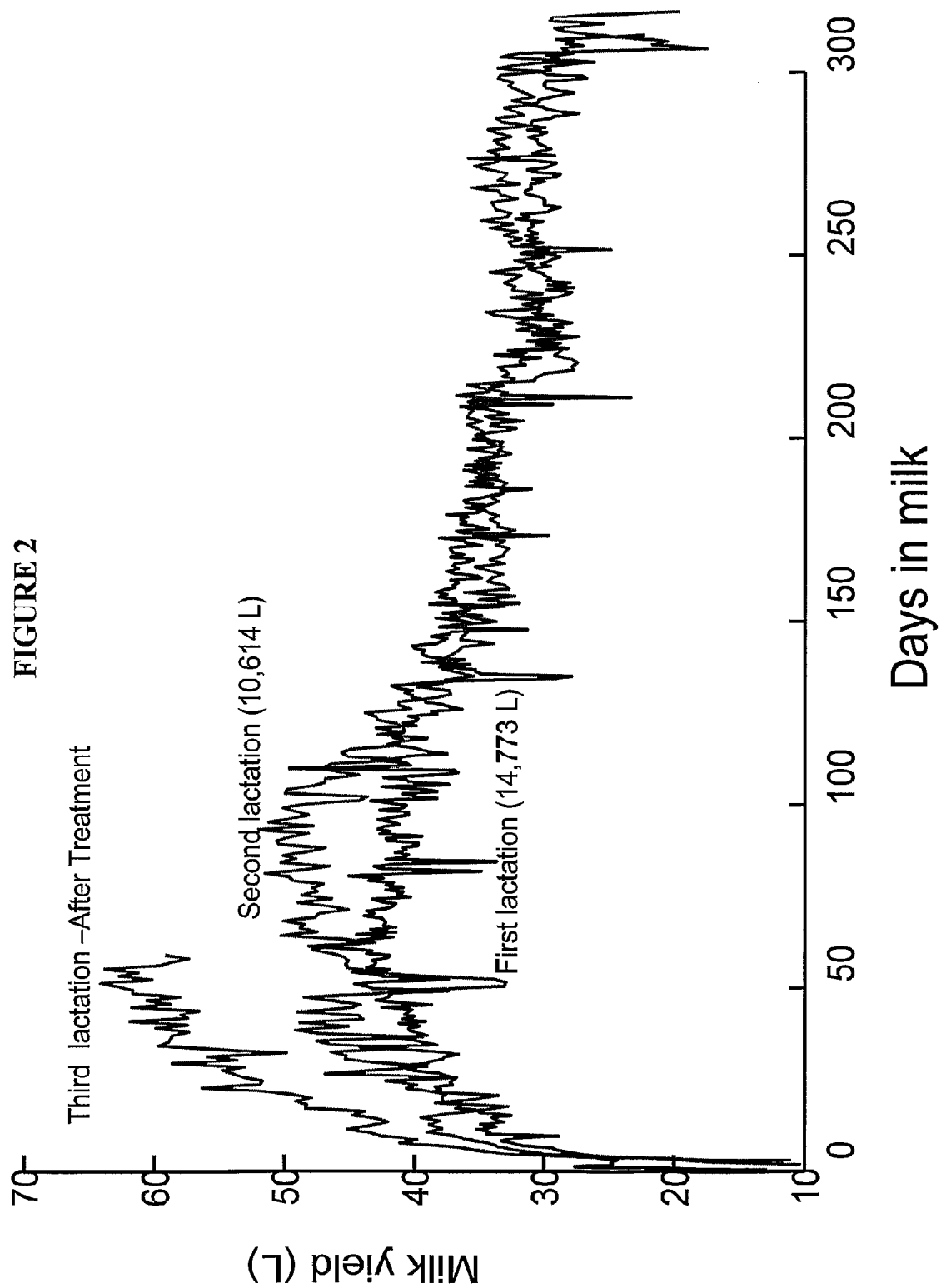
FIG. 2 shows the increase in milk production of cow No. 2331 after administration of casein hydrolyzate compared to previous lactation periods.

FIGS. 1 and 2 depict typical response to casein hydrolyzate (cow No. 2425 and 2331 respectively). Both cows were infected with *Staphylococcus aureus* at the time of treatment. It can be seen, that the infection caused a decrease in milk yield production during the second lactation period. After the treatment, however, the milk yield has increased significantly from parturition until the last measurement (60 days after parturition). Table 9 shows that the increase in milk yield does not negatively affect the milk quality, measured by protein and fat concentration.

TABLE 9

Effect of treatment with casein hydrolyzate on proteins and fat concentration in the milk obtained after parturition up to 100 days of lactation.

| | Control | | Treated | |
| --- | --- | --- | --- | --- |
| | Before treatment | After treatment | Before treatment | After treatment |
| Protein (%) | 3.0 | 2.9 | 3.1 | 3.2 |
| Fat (%) | 3.5 | 3.6 | 3.5 | 3.3 |

Example 5.2

Effect of Single Applications of Casein Hydrolyzate

The aim of this experiment was to study the effect of a single treatment with casein hydrolyzate, applied to four glands at dry-off before parturition on the post-calving milk yield. The importance of a regime of a single application resides in reduction of the workload in a farm and in the compliance of the stuff to the treatment administration.

Holstein cows (55), being at least at the second lactating period, from one dairy herd participated in the experiment from Jul. 25, 2005 to Nov. 11, 2005.

Study cows, inclusion and exclusion criteria, milk sampling, bacteriologic tests, and study protocols are similar to Example 2.2 and 4.2. Individual cow milk yield was automatically recorded thrice daily. The effect of casein hydrolyzate on post calving milk yield (from 4 to 103 days) was assessed by comparing the milk yield at the following defined periods:

| Period 1 | Period 2 | Period 3 |
|---|---|---|
| 3 to 103 d | last 120 d | 3 to 103 d |
| Calving Concurrent Lactation | Treatment with CNH Dry Period | Calving Lactation |

The milk yield of period 3 was compared to the milk yield of periods 1 and 2 (See the above scheme for the definition of periods).

The cows participated in the study were at a different stages regarding number of parturition, and, accordingly, number of lactation. Standardization of milk yield between cows at different lactations was corrected according to milk yield of the lactation number as described in Example 3 hereinabove. Twenty-eight cows were treated at the end of the first lactation, 17 at the end of the second and 10 at the end of the third or more lactation. Milk yield in liters is presented as crude results and after standardization. The data were analyzed by SAS/STAT package as described in example 5.1.

Results

Data were collected from 55 cows. Milk yield in period 3 increased by 11.60% ($p<0.01$) in comparison to milk yield in period 1 (Table 10).

TABLE 10

Effect of casein hydrolyzate treated as a single dose at dry off on milk yield after parturition

| Days from calving date | Period 1 | | Period 3 | |
|---|---|---|---|---|
| | Crude | After Correction | Crude | After Correction |
| 4-23 | 33.09 | 37.22 | 42.88 | 43.63 |
| 24-43 | 38.39 | 43.20 | 48.86 | 49.72 |
| 44-63 | 39.82 | 44.85 | 48.90 | 49.77 |
| 64-83 | 39.08 | 44.08 | 47.75 | 48.61 |
| 84-103 | 38.93 | 43.97 | 46.60 | 47.45 |
| 4-103 | 37.86 | 42.66 | 46.79 | 47.61 |

In cows having intramammary infection (IMI) (n=13, glands=19) the effect of casein hydrolyzate treatment was more prominent ($p<0.01$) because daily milk quantity in period 2 (Table 11) was 2.2 liters lower compared to the milk amount obtained from cows with no IMI, whereas in period 3 milk yield of cows having IMI and cows with no IMI was similar (Table 12).

TABLE 11

Milk yield in period 2 in IMI and non-IMI.

| Days previous to dry-off | IMI Cows | | Non-IMI Cows | |
|---|---|---|---|---|
| date | Crude | After Factorization | Crude | After Factorization |
| 120-101 | 32.05 | 36.49 | 33.44 | 37.90 |
| 100-81 | 31.31 | 35.69 | 32.18 | 36.54 |
| 80-61 | 28.50 | 32.62 | 30.64 | 34.84 |
| 60-41 | 26.39 | 30.22 | 28.79 | 32.80 |
| 40-21 | 24.51 | 28.14 | 26.39 | 30.14 |
| 20-1 | 21.74 | 24.98 | 23.10 | 26.45 |
| 120-1 | 27.42 | 31.36 | 29.09 | 33.11 |

TABLE 12

Effect of casein hydrolyzate treated as a single dose at dry off on milk yield after parturition (period 3)

| Days After Calving date | Period 3 from IMI Cows in Period 2 | | Period 3 from non-IMI Cows in Period 2 | |
|---|---|---|---|---|
| | Crude | After Standardization | Crude | After Standardization |
| 4-23 | 41.69 | 42.39 | 42.67 | 43.43 |
| 24-43 | 47.54 | 48.29 | 49.28 | 50.17 |
| 44-63 | 49.61 | 50.41 | 48.68 | 49.57 |
| 64-83 | 48.90 | 49.71 | 47.38 | 48.26 |
| 84-103 | 47.14 | 47.92 | 46.43 | 47.30 |
| 4-103 | 46.97 | 47.74 | 46.73 | 47.57 |

Example 6

Effect of Casein Hydrolyzed on the Welfare of Cows Induced to Dry Off

According to standard practices, modern dairy cows are dried 60 days before the expected parturition as a compromise between the farmer's wish to maximize milk production and the need for a minimal "dry off period" that would prevent a decline in milk production in the next lactation (Annen et al., 2004, ibid). This practice is associated with abrupt cessation of milking of cows still producing considerable amounts of milk, 20 to 40 liters per day and sometimes-even 50 liters per day. Such a practice results in accumulation of massive amounts of milk in the udder and is associated with udder engorgement and milk leakage, which causes frequently noticeable agony to the cow associated with loud screaming for several days. Thus, the current practice to dry off cows in modern dairy farming hampers considerably the welfare state of cows.

The aim in this experiment is to test the influence of treatment with casein hydrolyzed on the behavior and welfare of producing dairy cows induced into dry-off by abrupt cessation of milking.

20 Holstein cows toward the end of lactation (~60 days) and producing 17-35 liters milk per day were entered to the study. Cows were paired according to lactation number, days in milk, days to parturition, teat-end integrity, milk yield, SCC per ml of milk per cow or quarter and number of quarters infected at day of drying-off (Table 13).

TABLE 13

Comparison of the start point for case cows (CNH + Cefquinome) and control (Cefquinome) cows (n = 10 for each group, the data is presented as mean ± SD).

| | Case Cows CNH + Cefquinome | | Control Cows Cefquinome | |
|---|---|---|---|---|
| | Mean ± SD | Range | Mean ± SD | Range |
| Lactation number | 1.7 ± 0.7 | 1-3 | 1.9 ± 0.9 | 1-3 |
| Days in milk | 355.8 ± 58.4 | 285-451 | 327.0 ± 39.8 | 281-388 |
| Days to parturition | 59.3 ± 9.8 | 42-70 | 61.2 ± 10.6 | 38-75 |
| Teat-end integrity | 1.3 ± 0.7 | 0-2 | 1.2 ± 0.7 | 0-2 |
| Milk yield (kg/day) | 25.1 ± 5.3 | 17-32 | 26.4.1 ± 5.2 | 21-35 |
| SCC (×1000) | 171.6 ± 219.9 | 41-704 | 205.8 ± 250.6 | 54-900 |
| Bacterial infection status (cow; quarters)* | 4; 4 | | 4; 6 | |

Quarter's milk SCC and bacterial isolation were tested a week apart for 3 times, before drying-off. One cow of each pair was then assigned to a subgroup randomly (by flipping a coin). Cows in subgroup 1 were treated after milking with casein hydrolyzate and with the broad range antibiotic Cefquinome, (75 mg per dose) (N+C), while the cows in subgroup 2 were treated with Cefquinome alone (75 mg per dose) (C). The cows of the 2 subgroups were housed together for adjustment in a confined shelter providing 10 square meter shaded slatted floor and 10 square meter of concrete surfaced yard for each cow For one week before treatment, and then remained in that place for 2 weeks thereafter. After the three weeks, from a week before treatment to the end of the second week after treatment, the cows ware a computerized leg-mounted sensor (Afifarm Management System, S.A.E. Afikim, Israel), which enables monitoring, registering and transmitting animal activity (foot steps) and lying behavior (LB), with minimal disturbance to other free animal behavior.

Udder pressure index (UPI) was set as follows: 0, 1, 2 and 3, where 0 is no pressure, 1 is medium pressure, 2 is high pressure and 3 is extremely high pressure. Arbitrary UPI values were determined by assessing the udder pressure by pressing a finger into the tissue and assessing its resistant to pressure in two areas, the milk cistern and *corpus ubeis*, 10 cm above the teats. All measurements of UPI were carried out by the same trained person once a day at the same hour throughout the experiment.

Data were statistically analyzed using the fit model procedure for repeated measurements of JMP (Version 5, SAS Institute, Cary, N.C.); treatment was the between-subject factor and time was the within-subject factor. Differences were considered significant at P<0.05. The model was:

$$Y_{ijklm} = \mu + Pi + \alpha j + C(ij)k + \gamma + \alpha\gamma il + \epsilon_{ijklm}$$

where $Y_{ijklm}$=the dependent variable, $\mu$=overall mean, $P_i$=fixed effect of period (pre- and post-dry off; i=1 to 2), $\alpha_j$=fixed treatment effect i (I=1 to 2), $C_{(ij)k}$=random effect of cow k (k=1 to 10) within period i and treatment j; $\gamma_l$=effect of day 1 (1=1 to 9); $\alpha\gamma il$=effect of interaction of treatment j and day 1; and $\epsilon_{ijklm}$=random error associated with cow k in period i and treatment j at day 1.

Comparisons between treatments for period, or for specific day post-treatment were made by t-test using the Tukey-Kramer HSD.

In addition, a linear regression analysis was carried out for each treatment separately in two cases: (i) days in experiment as independent variable vs. accumulative number of steps, and (ii) $\Delta$ (where $\Delta$ refers to the difference of data measured at a given day post-calving minus the average of the same data during pre-calving) of UPI as an independent variable vs. $\Delta$ of the ratio between number of steps and duration of lying. The significance of the regression was evaluated from the regression coefficient and n, whereas differences between regression slopes was evaluated from the regression slope (b), standard error of the slope ($S_b$) and n by t-test.

Figure 3:
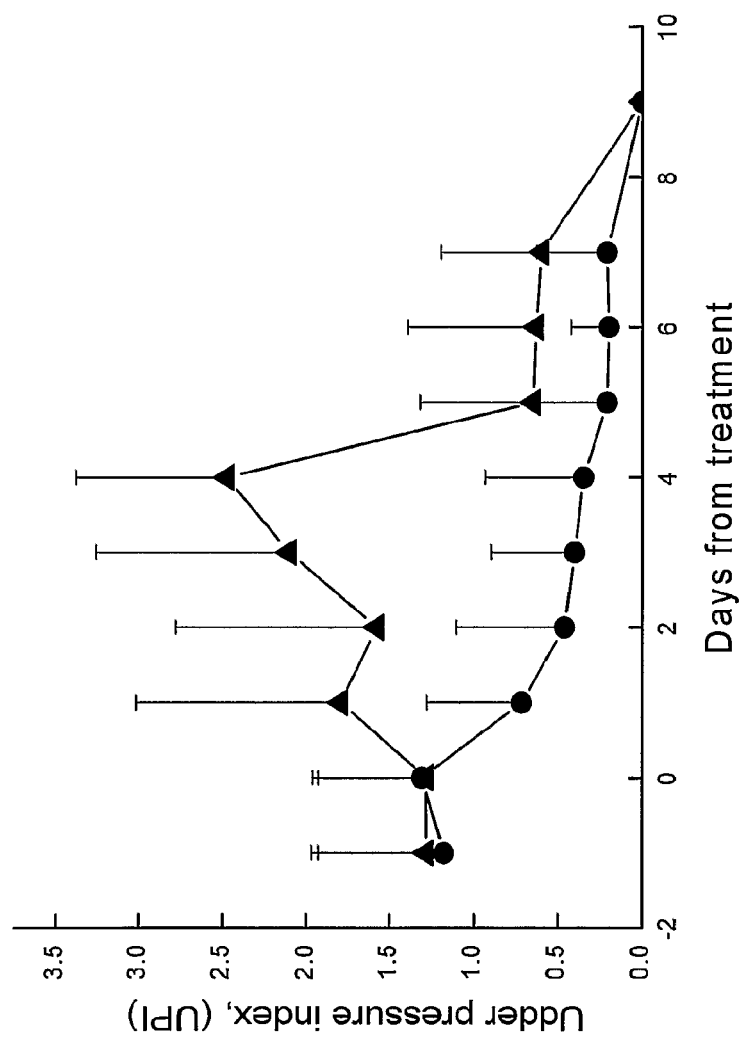
FIG. 3 shows the udder pressure index of 10 cows that received treatment (abrupt cessation of milking+antibiotic dry treatment+casein hydrolyzate treatment) and 10 control cows dried off in the conventional way (abrupt cessation of milking+antibiotic dry treatment) during the last 3 days of lactation (Lactation) and the first seven days after being dried off. The differences between treatments at the post-drying period were significant at $P<0.01$.
Figure 4B:
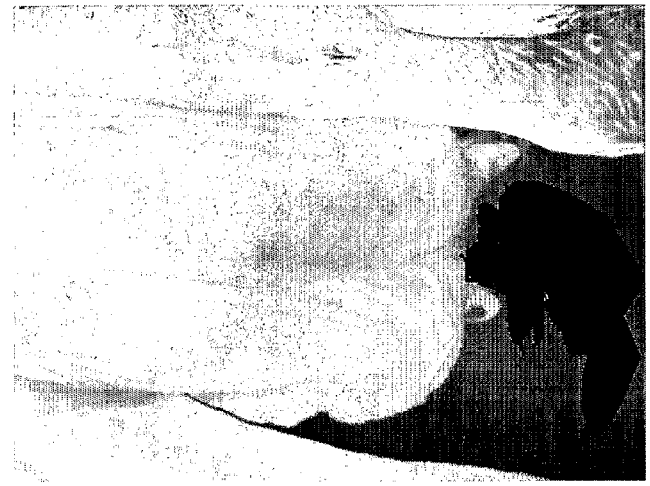
FIG. 4 shows udder of 2 cows on day 4 post treatment with milk yield over 30 L.
FIG. 4A—cow treated with C (abrupt cessation of milking+antibiotic dry treatment) FIG. 4B—cow treated with C+N (abrupt cessation of milking+casein hydrolyzate+antibiotic dry treatment).
Figure 4A:

The UPI arbitrary values (FIG. 3) increased markedly from ~1.2 before treatment to values in the range of 1.8 to 2.5 in the cows treated only with antibiotic (C), in comparison with a sharp drop in the N+C treated cows during the first 4 days after inducing the cows into involution, thus, during these 4 days the UPI values were significantly different between the groups (p<0.01). Only following the $5^{th}$ day after being induced into dry-off, UPI of the control cows declined. FIG. 4 presents the photographs of the udder of 2 cows on day 4 after treatment. The milk yield of these particular two cows was over 30 liters per day dry-off. The picture in FIG. 3 demonstrate the differences between treated cow with UPI=0 (panel B), and that of untreated cow, with UPI=~2 (panel A).

Figure 5:
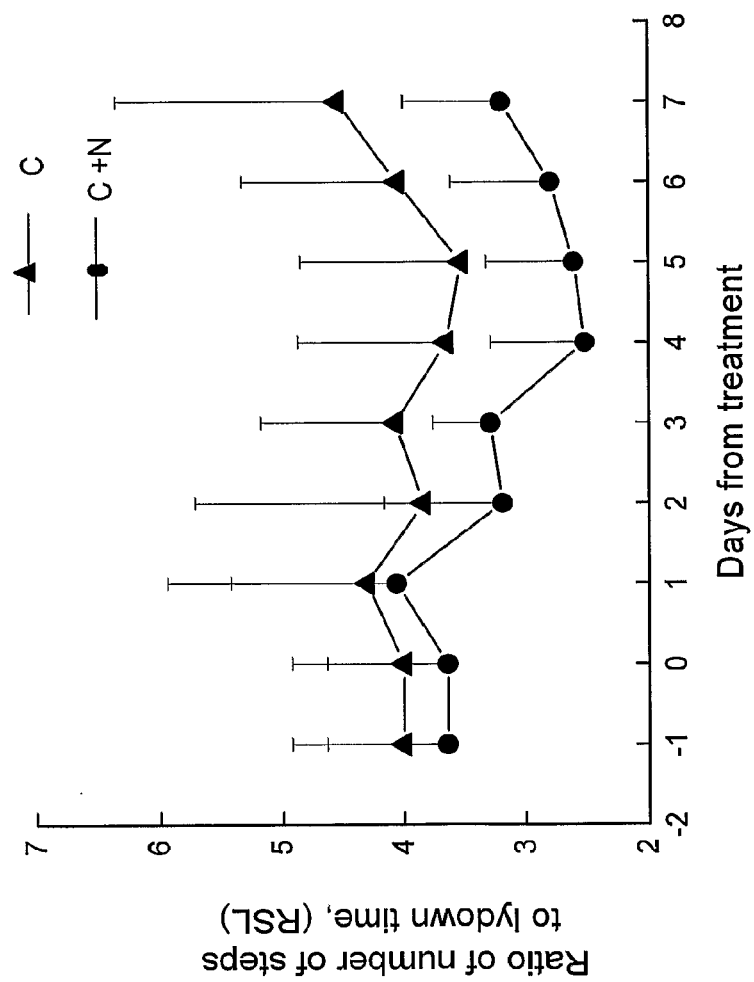
FIG. 5 shows the average accumulative ratio between number of steps and lie down duration of 10 cows that received treatment (C+N–abrupt cessation of milking+antibiotic dry treatment casein hydrolyzate treatment) and 10 control cows dried off in the conventional way (C–abrupt cessation of milking+antibiotic dry treatment) during the last 3 days of lactation (Lactation) and the first seven days after being dried off. The differences between treatments at the post-drying period were significant at $P<0.005$.

The ratio between number of steps and duration of lying (RSL) was used as a mean to assess "animal comfort" (FIG. 5). The ratio become smaller for N+C treated cows, starting from the second day after treatment while in the C treated cows the ratio was unchanged. As a result, the difference between the groups widened and became significant (p<0.005) from the $3^{rd}$ day after treatment and onward.

All in all, the udder pressure, the activity and rest behavior of cows treated with casein hydrolyzate were clearly associated with signs that the cows did not suffer and that they were calmer and more comfortable than cows induced into dry off by the conventional method.

While the certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

What is claimed is:

1. A method for reducing the length of the dry period between cycles of lactation in a lactating animal without negatively affecting the milk yield, comprising administering to the lactating animal a composition comprising a therapeutically effective amount of at least one phosphopeptide derived from casein, wherein the at least one phosphopeptide comprises the amino acid sequence Ser(p)-Ser(p)-Ser(p)-Glu-Glu (SEQ. ID NO:1) having an average molecular weight of from about 1,000 to about 5,000 Dalton, thereby reducing the length of said dry period between cycles of lactation in said lactating animal without negatively affecting the milk yield.

2. The method of claim 1, wherein the length of the dry period is reduced to less than 50 days.

3. The method of claim 2, wherein the length of the dry period is reduced to between about 20 days to about 30 days.

4. The method of claim 1, wherein the at least one phosphopeptide is selected from the group consisting of a phosphopeptide derived from β-casein comprising the amino acid sequence as set forth in SEQ ID NO:2; a phosphopeptide derived from αS1-casein comprising the amino acid sequence as set forth in SEQ ID NO:3; a phosphopeptide derived from αS2-casein comprising the amino acid sequence as set forth in SEQ ID NO:4; and a phosphopeptide derived from αS2-casein comprising the amino acid sequence as set forth in SEQ ID NO:5.

5. The method of claim 1, wherein the at least one phosphopeptide derived from casein is selected from the group consisting of a phosphopeptide obtained by hydrolysis of casein and a synthetic phosphopeptide.

6. The method of claim 1, wherein the composition is administered into at least one mammary gland of the lactating animal.

7. The method of claim 6, wherein the composition is administered into the teat canal of the mammary gland.

8. The method of claim 1, wherein the composition is administered at the same time of the cessation of milking.

9. The method of claim 1, wherein the composition is administered between one to five times at intervals of from about 6 hours to about 24 hours.

10. A method for increasing the milk yield of a livestock lactating animal after parturition compared to the milk yield of the lactating animal before parturition, comprising administering to the lactating animal a composition comprising a therapeutically effective amount of at least one phosphopeptide derived from casein, wherein the at least one phosphopeptide comprises the amino acid sequence Ser(p)-Ser(p)-Ser(p)-Glu-Glu (SEQ. ID NO:1) having an average molecular weight of from about 1,000 to about 5,000 Dalton, thereby increasing the milk yield of said livestock lactating animal after parturition compared to the yield before parturition.

11. The method of claim 10, wherein the average increase in the milk yield is at least about 3% in the first 100 days after parturition.

12. The method of claim 10, wherein the parturition is subsequent to a dry period.

13. The method of claim 10, wherein the at least one phosphopeptide is selected from the group consisting of a phosphopeptide derived from β-casein comprising the amino acid sequence as set forth in SEQ ID NO:2; a phosphopeptide derived from αS1-casein comprising the amino acid sequence as set forth in SEQ ID NO:3; a phosphopeptide derived from αS2-casein comprising the amino acid sequence as set forth in SEQ ID NO:4; and a phosphopeptide derived from αS2-casein the amino acid sequence as set forth in SEQ ID NO:5.

14. The method of claim 10, wherein the at least one phosphopeptide derived from casein is selected from the group consisting of a phosphopeptide obtained by hydrolysis of casein and a synthetic phosphopeptide.

15. The method of claim 10, wherein the composition is administered into at least one mammary gland of the lactating animal.

16. The method of claim 15, wherein the composition is administered into the teat canal of the mammary gland.

17. The method of claim 10, wherein the composition is administered at the same time of the cessation of milking.

18. The method of claim 10, wherein the composition is administered between one to five times at intervals of from about 6 hours to about 24 hours.

19. A method for increasing milk hygiene of a lactating animal, comprising administering to a mammary gland of the lactating animal a composition comprising a therapeutically effective amount of at least one phosphopeptide derived from casein, as to reduce in the next lactating period after a dry period the somatic cell counts (SCC) in the milk as compared to the SCC before peptide administration, wherein the at least one phosphopeptide comprises the amino acid sequence Ser(p)-Ser(p)-Ser(p)-Glu-Glu (SEQ. ID NO:1) having an average molecular weight of from about 1,000 to about 5,000 Dalton.

20. The method of claim 19, wherein the somatic cell counts in the milk is reduced to less than 400,000 cells/ml.

21. The method of claim 19, wherein the at least one phosphopeptide is selected from the group consisting of a phosphopeptide derived from β-casein comprising the amino acid sequence as set forth in SEQ ID NO:2; a phosphopeptide derived from αS1-casein comprising the amino acid sequence as set forth in SEQ ID NO:3; a phosphopeptide derived from αS2-casein comprising the amino acid sequence as set forth in SEQ ID NO:4; and a phosphopeptide derived from αS2-casein comprising the amino acid sequence as set forth in SEQ ID NO:5.

22. The method of claim 19, wherein the at least one phosphopeptide derived from casein is selected from the group consisting of a phosphopeptide obtained by hydrolysis of casein and a synthetic phosphopeptide.

23. The method of claim 19, wherein the composition is administered into at least one mammary gland of the lactating animal.

24. The method of claim 23, wherein the composition is administered into the teat canal of the mammary gland.

25. The method of claim 19, wherein the composition is administered at the same time of the cessation of milking.

26. The method of claim 19, wherein the composition is administered between one to five times at intervals of from about 6 hours to about 24 hours.

27. The method of claim 1, wherein the composition is substantially devoid of micelles.

28. The method of claim 1, wherein the composition is administered by topical application.

29. The method of claim 1, wherein the composition is administered in combination with anti-microbial therapy, selected from the group consisting of: antibiotic treatment, bactericide treatment, steroidal and non-steroidal anti-inflammatory treatment, treatment with an immunomodulator, and vaccination.

30. The method of claim 10, wherein the composition is substantially devoid of micelles.

31. The method of claim 10, wherein the composition is administered during the dry period.

32. The method of claim 10, wherein the composition is administered by topical application.

33. The method of claim 10, wherein the composition is administered in combination with anti-microbial therapy, selected from the group consisting of: antibiotic treatment, bactericide treatment, steroidal and non- steroidal anti-inflammatory treatment, treatment with an immunomodulator, and vaccination.

34. The method of claim 19, wherein the composition is substantially devoid of micelles.

35. The method of claim 19, wherein the composition is administered during the dry period.

36. The method of claim 19, wherein the composition is administered by topical application.

37. The method of claim 19, wherein the composition is administered in combination with anti-microbial therapy, selected from the group consisting of: antibiotic treatment, bactericide treatment, steroidal and non-steroidal anti-inflammatory treatment, treatment with an immunomodulator, and vaccination.

* * * * *